United States Patent
Vasileiadis et al.

(10) Patent No.: US 6,919,062 B1
(45) Date of Patent: Jul. 19, 2005

(54) PERMREACTOR AND SEPARATOR TYPE FUEL PROCESSORS FOR PRODUCTION OF HYDROGEN AND HYDROGEN, CARBON OXIDES MIXTURES

(75) Inventors: Savvas Vasileiadis, North Hills, CA (US); Zoe Ziaka, North Hills, CA (US)

(73) Assignees: Savvas P. Vasileiadis, North Hills, CA (US); Ph.D. Chemical Engineering, Ithaca, NY (US)

( * ) Notice: Subject to any disclaimer, the term of this patent is extended or adjusted under 35 U.S.C. 154(b) by 0 days.

(21) Appl. No.: 09/525,176

(22) Filed: Mar. 14, 2000

Related U.S. Application Data

(63) Continuation-in-part of application No. 08/595,040, filed on Jan. 31, 1996, now Pat. No. 6,090,312.

(51) Int. Cl.⁷ .......................... C01B 31/20; C01B 3/22; C01B 3/26
(52) U.S. Cl. ............... 423/437.1; 423/648.1; 423/650; 423/651; 423/652
(58) Field of Search ................. 585/252, 257, 585/263, 911; 423/650, 651, 652, 653, 654, 655, 656, 359, 360, 437.1, 648.1; 252/373; 165/104.12; 422/239; 429/20, 19

(56) References Cited

U.S. PATENT DOCUMENTS

| | | | | |
|---|---|---|---|---|
| 3,950,447 A | * | 4/1976 | Gryaznov .................... | 260/667 |
| 4,423,022 A | * | 12/1983 | Albano et al. ............... | 423/360 |
| 4,713,234 A | | 12/1987 | Weirich et al. ......... | 423/648 R |
| 4,810,485 A | | 3/1989 | Marianowski et al. ... | 423/648.1 |
| 5,198,310 A | * | 3/1993 | Fleming et al. ............... | 429/17 |
| 5,229,102 A | | 7/1993 | Minet et al. ................. | 423/652 |
| 5,637,259 A | | 6/1997 | Galuszka et al. ........... | 252/373 |
| 5,639,431 A | | 6/1997 | Shirasaki et al. ........... | 422/212 |
| 5,658,681 A | | 8/1997 | Sato et al. ...................... | 429/13 |
| 5,861,137 A | | 1/1999 | Edlund et al. ............... | 423/652 |
| 5,935,533 A | * | 8/1999 | Kleefisch et al. ........... | 422/211 |
| 5,938,800 A | | 8/1999 | Verrill et al. ............... | 48/127.9 |
| 6,274,260 B1 | * | 8/2001 | Schuler ........................ | 429/19 |
| 2001/0009653 A1 | * | 7/2001 | Clawson .................. | 423/437.1 |

FOREIGN PATENT DOCUMENTS

| | | | | |
|---|---|---|---|---|
| JP | 4-182302 A | * | 6/1992 | ............. C01B/3/38 |

OTHER PUBLICATIONS

S.Vasileiadis and Z. Ziaka, "Environmentally Benign Hydrocarbon Processing Applications of Single and Integrated Permreactors", in Reaction Engineering for Pollution Prevention pp. 247–304, Elsevier Science (2000).

(Continued)

*Primary Examiner*—Wayne A. Langel
(74) *Attorney, Agent, or Firm*—Savvas P. Vasileiadis

(57) ABSTRACT

Overall permreactor-separator process designs and effective permreactor designs with increased mass and heat transfer, reactant conversion, product yield and optional recycling for processing methane, hydrocarbons, alcohols, carbon monoxide, natural gas, acidic natural gas, cool gas, biomass gas, and mixtures of hydrocarbons with carbon dioxide, based on the reforming reactions of these feedstocks with steam and carbon dioxide and the dehydrogenation reactions of saturated hydrocarbons. Final exit streams from these gas phase processors contain pure hydrogen, hydrogen and carbon monoxide mixture, hydrogen and carbon dioxide mixture, and can be used as a direct feed in molten carbonate, solid oxide, proton exchange membrane, alkaline, phosphoric acid and other types of hydrogen driven fuel cells. Same final exit processed streams can be alternatively used for direct chemical synthesis such as methanol, for hydrogenations and hydrogen based reduction reactions such as those of unsaturated hydrocarbons to paraffins, and as feed in power generation systems such as gas turbines and gas engines.

48 Claims, 13 Drawing Sheets

OTHER PUBLICATIONS

Alternative generation of $H_2$, CO and $H_2$, $CO_2$ mixtures from steam–carbon dioxide reforming of methane and the water gas shift with permeable (membrane) reactors, S. Vasileiadis et al., *Chem. Eng. Comm.*, vol. 176, pp. 247–252, (1999).

Reactor–Membrane permeator cascade for enhanced recovery and production of $H_2$ and $CO_2$ from the catalytic methane steam reforming reaction, Z. Ziaka et al., *Chem. Eng. Comm.*, vol. 156, 161, (1997).

Novel reactor–membrane permeator methane–steam reforming process for enhanced recovery of $H_2$ and $CO_2$, Z. Ziaka et. al., 5th World Congress in Chemical Engineering, Symposium Series, San Diego, CA Jul. (1996).

N. Itoh et al., "Development of a novel oxidative palladium membrane reactor", AIChE Symp. Ser., No. 268, vol. 85, 10 (1989).

R. Zhao et al., "Studies on palladium membrane reactor for dehydrogenation reaction", *Sep. Sci.&Tech.*, 25(13–15), 1473 (1990).

M. Oertel et al., *Chem. Eng. Technol.*, 10,248 (1987).

Introductory permreactor, permeator hydrocarbon, carbon oxide processors for externally reformed–(gas phase) fuel cell systems, S. Vasileiadis and Zoe Ziaka, submitted for publication, Aug. 1999.

Polymer membrane reactors for enhanced hydrocarbon conversion and upgrading, S. Vasileiadis and Zoe Ziaka, Invention Disclosure Document #414880, marked Mar. 6, 1997.

\* cited by examiner

PERMREACTOR AND SEPARATOR TYPE FUEL PROCESSORS FOR PRODUCTION OF HYDROGEN AND HYDROGEN, CARBON OXIDES MIXTURES

CROSS REFERENCE TO RELATED APPLICATIONS

Continuation in part of Ser. No. 08/595,040, filed Jan. 31, 1996, now U.S. Pat. No. 6,090,312 (issued Jul. 18, 2000).

STATEMENT REGARDING FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON COMPACT DISC

Not Applicable

BACKGROUND OF THE INVENTION

1. Field of the Invention

This invention relates to new process and reactor designs including permeable reactors (permreactors) and permeators for the hydrocarbon steam reforming, hydrocarbon carbon dioxide reforming, combined hydrocarbon steam and carbon dioxide reforming, alcohol steam reforming, water gas shift, paraffin dehydrogenation, methanol synthesis, and combination of these conversion reactions for production of valuable fuels and chemicals. It also relates to the utilization of the end reaction products such as pure hydrogen, hydrogen and carbon monoxide, hydrogen and carbon dioxide, and mixtures of these species, into specific applications such as fuel cells, gas turbines, gas engines and synthesis reactors.

2. Description of the Related Art Including Information Disclosed Under 37 CFR 1.97 and 1.98

This current invention describes new and improved process and reactor designs which involve permeable reactors (permreactors) and permeators for the hydrocarbon steam reforming, hydrocarbon carbon dioxide reforming, combined hydrocarbon steam and carbon dioxide reforming, alcohol steam reforming, the water gas shift reaction, dehydrogenation reactions of hydrocarbons, such as dehydrogenation of alkanes (i.e., paraffins) to alkenes, and combination of these previous reactions.

The reactions and heats of reactions that are referred to and utilized within the embodiments of the invention are well known and are listed below:

(1) $CH_4 + H_2O = CO + 3H_2$ ($\Delta H^\circ_{298} = 206.1$ kJ/mol), methane-steam reforming (2) $CH_4 + CO_2 = 2CO + 1H_2$ ($\Delta H^\circ_{298} = 247.3$ kJ/mol), methane-$CO_2$ reforming (3) $CO + H_2O = CO_2 + H_2$ ($\Delta H^\circ_{298} = 41.15$ kJ/mol), water gas shift (4) $C_nH_{2n+2} = C_nH_{2n} + H_2$ (endothermic dehydrogenation reactions, heat of reaction varies depending on the type of feedstock processed in the reactor, e.g., ethane, propane, butane, pentane)

(5) $CO + 2H_2 = CH_3OH$ ($\Delta H^\circ_{298} = -128.2$ kJ/mol), methanol synthesis (6) $CO_2 + 3H_2 = CH_3OH + H_2O$ ($\Delta H^\circ_{298} = -49.5$ kJ/mol), methanol synthesis (7) $CH_3OH + H_2O = CO_2 + 3H_2$ ($\Delta H^\circ_{298} = 49.5$ kJ/mol), methanol-steam reforming These are catalytic reactions utilizing catalysts such as nickel (Ni), ruthenium (Ru), rhodium (Rh), palladium (Pd), platinum (Pt), chromium (Cr), copper (Cu), zinc (Zn), Cobalt (Co), Gold (Au) and other metals, and bimetallic catalyst compositions of these metals. The catalysts are supported on alumina ($Al_2O_3$), titania ($TiO_2$), silica ($SiO_2$), zirconia ($ZrO_2$), lanthanum ($La_2O_3$) and other supports, enriched with earth metals such as Ca, La, Na, K.

Use of reactor and membrane permeator configurations and systems disclosed in our previous U.S. patent application Ser. No. 08/595,040, increase the overall process efficacy by increasing the total conversion of the following feedstocks: hydrocarbon, hydrocarbon-$CO_2$ mixtures, methane, methane-$CO_2$ mixtures, alcohols. Moreover, the yields to hydrogen and carbon monoxide or hydrogen and carbon dioxide are increased by the use of the integrated membrane permeators which separate effectively $H_2$ and $CO_2$ gases. Process efficiency is further improved by the recycling of unreacted and non-separated (non-permeated) hydrocarbon (e.g., methane) and carbon monoxide into the first (primary) reactor (reformer) or the alternative direction of the same stream into a consecutive catalytic reactor (reformer or water gas shift reactor) for additional production of hydrogen and carbon dioxide. Direct utilization of the produced and separated hydrogen, synthesis gas, and hydrogen-carbon dioxide mixtures from these processes into consecutive synthesis reactors, fuel cells and gas turbines and engines are additional advantages and continual applications of the proposed processes.

Current invention elaborates on the substitution of the primary conventional reactor (i.e., reformer, water gas shift, dehydrogenation reactor) by a permeable (membrane-type) reactor (so called permeator for simplicity) of specific design, and the correspondingly derived improved process and permeable reactor-separator configurations for the above mentioned reactions. Moreover, introduction and specification of double wall permreactors, besides the single wall permreactors, for conducting similar reactions are also disclosed. The described permreactors are designed to consist of interconnected parts which can be readily taken apart and assembled when service is necessary. For the disclosed integrated reaction-separation systems specific applications are disclosed such as the utilization of the end products and/or permeated (separated) streams into consecutively place synthesis reactors (including additional reformers or water gas shift reactors), gas turbines and engines, and various types of hydrogen based fuel cells and related fuel cell systems.

Previous reactor and permeable reactor designs from the above cited references refer mainly to methane and methanol steam reforming reactions but not to carbon dioxide reforming, water gas shift and dehydrogenation reactions as the present invention does. Moreover, previous inventions refer to a single reactor or permreactor or other reaction vessel instead of reactor-separator systems as the present invention describes. Present invention introduces double permeable-wall (double membrane-wall) reactors for hydrocarbon and alcohol processing reactions. The double membrane-wall reactors can be of various designs as disclosed within the embodiments of the invention. These can be catalytic reactors as adapted to specific process requirements in terms of setting key operating variables such as reaction temperature, pressure, space velocity, feed composition, to deliver final products (i.e., hydrogen and synthesis gas) in the purity and throughput required by consecutive applications. Moreover, flexibility in the selection of permreactor wall materials such as metals, inorganics, organics and composites, allows design of multifunctional permeable reactors which separate and deliver specific species (e.g., gases) with the required purity and throughput to consecutive applications. Flexibility in the selection of functional and specific permreactor wall materials for each process operation has also economic advantages. Current disclosed permreactor, separator, and overall process designs can utilize membrane materials selected from classes of metals, inorganics (non-porous or porous), polymers, carbons and carbonaceous materials, and composites. Therefore, the selection of less expensive membrane materials for a specific permreactor, permeator and process operation is available with current invented designs.

Present invention also teaches direct utilization of end product streams to consecutive synthesis reactors, fuel cells, gas turbines and gas engines. Present invention focuses on converting and upgrading primary hydrocarbon feedstocks such as methane, natural gas, coal gas, refinery feedstocks such as naphtha and alcohol feedstocks such as methanol and ethanol to higher calorific value hydrogen and carbon oxide mixtures; also it focuses on converting secondary and waste hydrocarbon feedstocks such as acidic natural gas, biomass gas to same valuable end products. Therefore, present invention describes environmentally benign reactor designs and process designs which abate and upgrade at the same time otherwise waste gases to valuable hydrogen, synthesis gas, hydrogen and carbon dioxide mixture. In situ conversion of carbon dioxide containing hydrocarbon mixtures and abatement of the carbon dioxide negative atmospheric and terrestrial greenhouse effect can be considered an additional benefit from the implementation of the invention.

BRIEF SUMMARY OF THE INVENTION

The present invention discloses double wall permeable reactors and the related elaborate reactor designs, which offer operational advantages by conducting in-situ reactions, in comparison with single wall permeable reactors and conventional non-permeable reactors. Consequently, three different permeable reactor configurations are disclosed. These reactor designs are applied to catalytic hydrocarbon and alcohol reforming, water gas shift and hydrocarbon dehydrogenation reactions. The first design is a double wall permreactor which consists of three concentric hollow cylindrical tubes with the two inner ones to be made by permeable metal, inorganic, carbon or polymer materials depending on the type of feedstocks used and the desired composition of final exit streams. Heating tubes run through the most-inner cylinder which is also filled with the main reaction catalyst. Similarly, the second reactor design consists also of three concentric hollow cylindrical tubes with the two inner ones to be made by permeable metal, inorganic, carbon or polymer materials but with the main reaction catalyst to be contained in the annular space between the most-outer and the next-inner tubes. Heating in this design is achieved by heating the external side of the most-outer tube. Third reactor design consists of an outer impermeable tube which nests multiple organic polymer or composite polymer tubes for gas permeation. Outer tube contains also the main reaction catalyst which is located around the polymer tubes. Heating is achieved by external heating of the outer tube. Moreover, the invention pertains to systems of the described permeable reactors with consecutive permeators for separation and further processing of post-reaction gases exiting from the reactors. Permeators can be made by polymer membranes for the concomitant separation of hydrogen and carbon dioxide gases or by metal, non-porous inorganic and carbon membranes for the separation of hydrogen only. These permreactor-permeator systems are applied to combined hydrocarbon stream and carbon dioxide reforming, hydrocarbon steam reforming, hydrocarbon carbon dioxide reforming, alcohol steam reforming, water gas shift and paraffin dehydrogenation reactions for increasing the reactant conversion and the yield to hydrogen, carbon monoxide and carbon dioxide. The separated hydrogen and carbon oxides are used in further chemical synthesis reactions and as fuel in fuel cells, gas turbines and gas engines.

The invention also includes hydrocarbon-$CO_2$-steam reforming systems of permreactors with cryogenic separators wherein the consecutive permeators are replaces by cryogenic separators and pure hydrogen and carbon monoxide are recovered as final products. Similar permreactors are also directly interconnected with solid oxide fuel cells for use of the products hydrogen, carbon monoxide and steam as direct fuel in the anode of the cell. Finally, the invention includes use of the disclosed permreactors in series with methanol synthesis and methanol reforming reactors for final production of methanol, hydrogen and carbon dioxide for use as synthesis chemicals or fuels. Detailed description of the invention are presented in the embodiments of the following Figures.

DETAILED DESCRIPTION OF THE INVENTION

Figure 1:
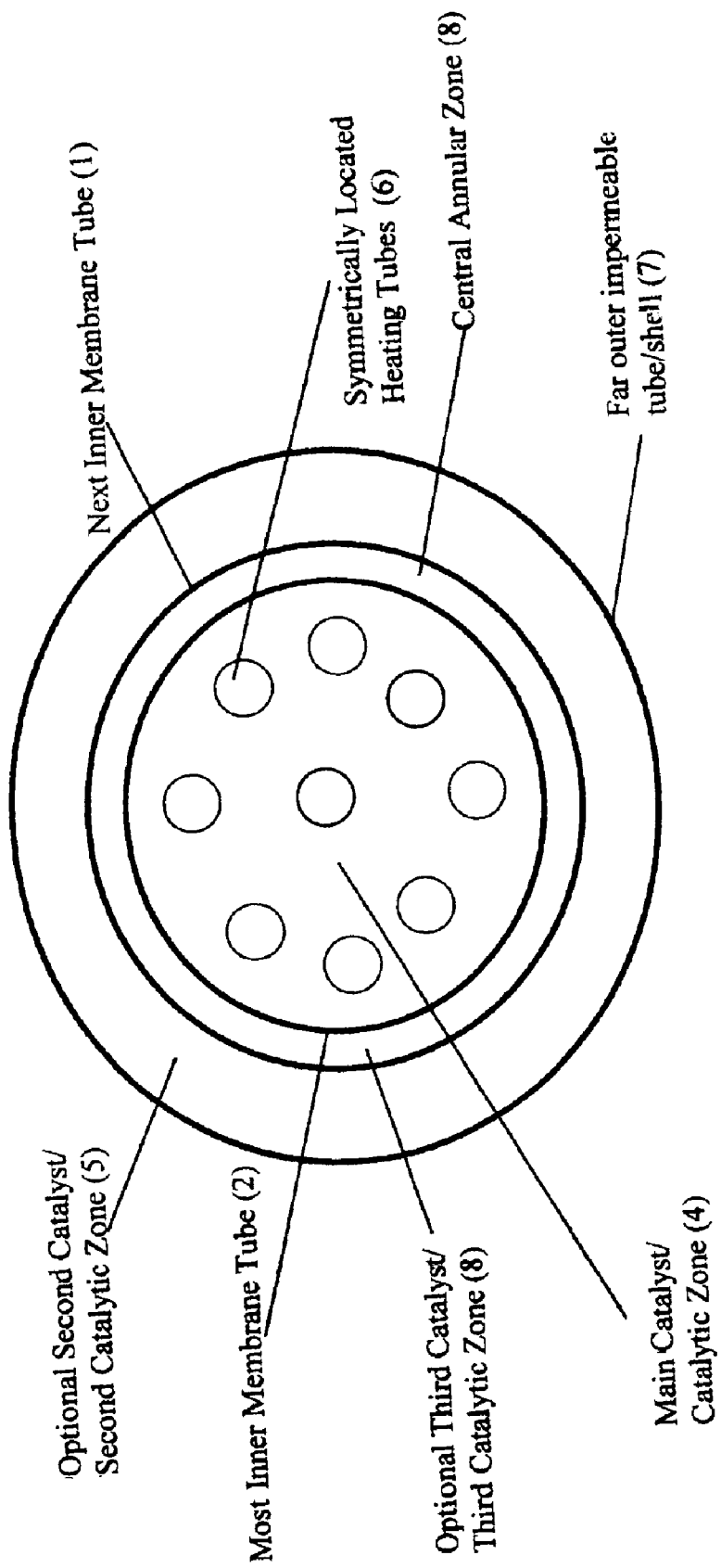
FIG. 1 shows the cross section of a concentric double permeable wall cylindrical reactor with tubular type heaters located along the catalyst zone, consisting of an inner metal, non-porous or porous inorganic, or carbon membrane tube and an outer membrane tube made by metal, non-porous inorganic, carbon or organic membrane enclosed within a far-outer impermeable tube.

FIG. 1 shows a cross section of the membrane reactor to be used in steam and carbon dioxide reforming of hydrocarbons, steam reforming of alcohols, water gas shift and dehydrogenation reactions, which consists of a concentric double wall cylindrical assembly with tubular type heaters located within the catalyst, along the catalyst zone. An outer impermeable tube (7) nests the two permeable concentric tubes. Reacting feedstocks such as steam and hydrocarbon, $CO_2$ and hydrocarbon, steam, $CO_2$ and hydrocarbon, steam and alcohols, or alkanes (paraffins) such as ethane, propane, n-butane, i-butane, pentane, naphtha and higher paraffins, and fed within the main catalyst zone (4) through special inlet fittings and they react in the catalyst to produce hydrogen, carbon monoxide, carbon dioxide. Optionally, small volumetric quantities of hydrogen can be added into above feedstocks to prevent heavy catalyst deactivation in the reactor inlet, wherein propensity for hydrocarbon cracking into carbon is high in absence of any hydrogen. The hydrocarbon reforming catalyst can be nickel, ruthenium, rhodium, palladium enriched with earth type metals such as potassium, calcium, magnesium, lanthanum, cerium, and supported on alumina, silica, titania, zirconia or other inorganic oxide. For the water gas shift reaction the catalytic metal can be nickel, also iron, copper, zinc, chromium, cobalt enriched with and supported on similar metal oxides. The methanol reforming catalysts can be zinc, chromium, copper, iron, nickel, ruthenium, rhodium palladium. Finally, the above described reactor design is applied as well for paraffin (alkane) dehydrogenation reactions and the reactor becomes a catalytic dehydrogenator which utilizes platinum, chromium, palladium catalysts enriched with and supported on similar inorganic oxides.

Hydrogen is removed along the inner membrane tube (2), wherein the membrane is made by a metal or inorganic (non-porous or porous), porous inorganic-metal or carbon material. Carbon monoxide, carbon dioxide, steam, hydrocarbons, alcohols may also permeate through first membrane in a lesser degree than hydrogen if the membrane is porous inorganic or inorganic-metal. An inert carrier gas such as argon, nitrogen, steam or a mixture of these gases may flow along the permeate annulus, between tubes (2) and (1), through suitable inlet fittings, to carry the permeate components at a specific pressure value. Permeate hydrogen is further removed through permeation along the outer membrane tube (1) so that permeated stream contains pure hydrogen only, with pure hydrogen to be used in various applications including feed to synthesis reactors, gas turbines and engines, and fuel cells. Outer membrane tube (1) is made by a metal, non-porous inorganic or carbon membrane which allows only hydrogen to permeate through, and therefore purifies hydrogen from the permeating carbon oxides, steam and hydrocarbons, in the annular zone between the two membrane tubes.

Metal materials permeable to hydrogen for the membrane tubes (1) and (2), include palladium, vanadium, and palladium alloys such as palladium-nickel, palladium-silver, palladium-zinc, palladium-chromium, palladium-copper, palladium-tungsten and others. Hydrogen permeable non-porous inorganic membranes include silicon carbide, silicon nitride, tungsten carbide, tungsten nitride, titanium carbide, titanium nitride, tantalum carbide, tantalum nitride and others. Porous inorganic membranes include alumina, silica, titania, zirconia, various types of glass and others. Carbon type membranes are made by deposition or other fabrication method (i.e., pyrolysis) of carbon or carbonaceous materials within a porous substrate to make it hydrogen permeable.

Metal and metal alloys can be deposited on porous inorganic or metal surfaces to make them hydrogen permeable. Palladium and other metal deposition as membranes can be done with electronics plating, electroplating, sputtering, chemical vapor deposition, physical vapor deposition and other applicable metal deposition or metallization techniques. Inorganic, inorganic-metal membrane materials can be deposited as well in porous inorganic or metal surfaces via various deposition techniques including incipient wetness, dip coating and sol gel methods.

Organic polymer, composite or copolymer membranes can be made by polymers such as polyimides, polycarbonates, polysulfones, polybenziimidazoles, polyphosphazenes, polyamides, polystyrenes, polycaprolactams, parylenes, polyvinyl halides, polyacetates, polysiloxanes and others to be permeable to hydrogen or to hydrogen and carbon dioxide. Finally, composites of the previous materials can be also made as hydrogen permeable membranes such as inorganic-metal, inorganic-organic, inorganic-metal-organic composites. Metal and metal alloy, non-porous inorganic and carbon membranes are highly selective to hydrogen, while porous inorganic, organic, and composite membranes are usually selective to other species as well. The disclosed double permeable wall reactor design can be fabricated by selecting among the aforementioned materials to satisfy process requirements for the reactor itself and the consecutive application processes disclosed later in the text.

The external space, created between the outer hydrogen permeable membrane tube (1) and the impermeable far outer shell (7), which receives the final permeate hydrogen, can be either empty, or may contain a selective catalyst (5) which converts permeate hydrogen after its combination with a component flowing in the external space parallel to the outer membrane tube. Such a flowing (sweep) component can be an unsaturated hydrocarbon (e.g., alkenes, alkynes) for conversion to saturated hydrocarbons after reaction with hydrogen, in an exothermic reaction. Flowing (sweep) component can be also carbon monoxide for direct production of methanol or gasoline (through Fischer-Tropsch synthesis) after combination with the permeate hydrogen in exothermic type reactions. Flowing gas can be nitrogen for exothermic ammonia synthesis after its combination with the permeate hydrogen. Other combination reactions of flowing species with permeate hydrogen can be these for reduction of aromatic hydrocarbons, also these for saturation of unsaturated alcohols, phenols, aldehydes, ketones acids, these for reduction of alkyl and aryl halides and these for reduction of nitroalkanes and aromatic nitro compounds to corresponding primary amines.

The heat generated by exothermic reactions in the external shell, may be transferred into the catalytic reaction zone of the inner membrane tube via the radial direction, thus providing part of the heat load necessary to drive the endothermic catalytic reactions in the inner membrane tube.

Permeation of reaction products through the membrane tubes, especially hydrogen through the inner membrane tube, shifts the thermodynamic equilibrium conversion of reactant species to the product side and produces excess hydrogen and carbon oxide products within the catalytic reaction zone (4). Outer membrane tube thereby, serves as a final permeable medium for the recovery of highly pure hydrogen product for use in hydrogen utilization applications. Outer metal membrane tube serves also as a separation medium for hydrogen out of the central annular zone between the two membrane tubes, so that partial pressure of hydrogen lowers substantially along the annular zone, and therefore continuous driving force exists for hydrogen permeation from the catalytic reaction zone (4) to the central annular zone (8). As an alternative to the invented design, for low operating gas reforming and dehydrogenation temperatures (e.g., between 200–400° C.) in the absence of steam as a reactant, the inner membrane tube (2) can be made by porous inorganic or inorganic-metal materials and the outer membrane tube (1) can be made by organic materials which withstand high temperature (i.e., materials with high glass transition temperature, Tg), and are permselective to both hydrogen and carbon dioxide which permeate through the inner tube (2) and flow along the central annular zone (8). The mixture of $H_2$ and $CO_2$ can be used directly in chemical synthesis applications such as this of alternative methanol synthesis via the reaction: $CO_2+3H_2=CH_3OH+H_2O$, and as direct feed in molten carbonate fuel cells via the overall electrochemical reaction: $H_2+CO_2+\frac{1}{2}O_2 \rightarrow H_2O+CO_2$. Moreover mixtures of $H_2$ and $CO_2$ can be converted to $CH_4$ or CO, if a special application requires, via the methanation or reverse water gas shift reactions respectively given below:

$$CO_2+4H_2=CH_4+2H_2O, \quad CO_2+H_2=CO+H_2O$$

The external (outer) membrane (1) serves also as a backup membrane medium in case the inner membrane develops cracks or defects and its permeability to various gases increases. In this case, the outer membrane will selectively separate specific gases based on the selected membrane material as described above. Moreover, operational and maintenance service for replacing old or damaged membrane and outer non-membrane tubes becomes easier with the proposed design, because each part of the reactor is interconnected with the rest and can be disassembled and assembled accordingly.

Heating of the reformer or reactor is achieved via tubes (6) arranged symmetrically around the reactor axis and operated in the gas combustion regime by flowing waste type hydrocarbons or hydrocarbon-hydrogen mixtures mixed with oxygen or air. Unreacted hydrocarbons, carbon monoxide, non-permeate hydrogen or any mixture of these species from the reformer outlet can be recycled as well into the heating combustion tubes (6). In an alternative heating configuration, a single cylindrical tube having the shape of a tube or a coil is located along the reactor axis and can be operated by using same quality of combusted gases. In a third alternative configuration the symmetrically located tubes with flowing gas can be replaced by cylindrical electric heaters, heating bars or coils.

Figure 2:
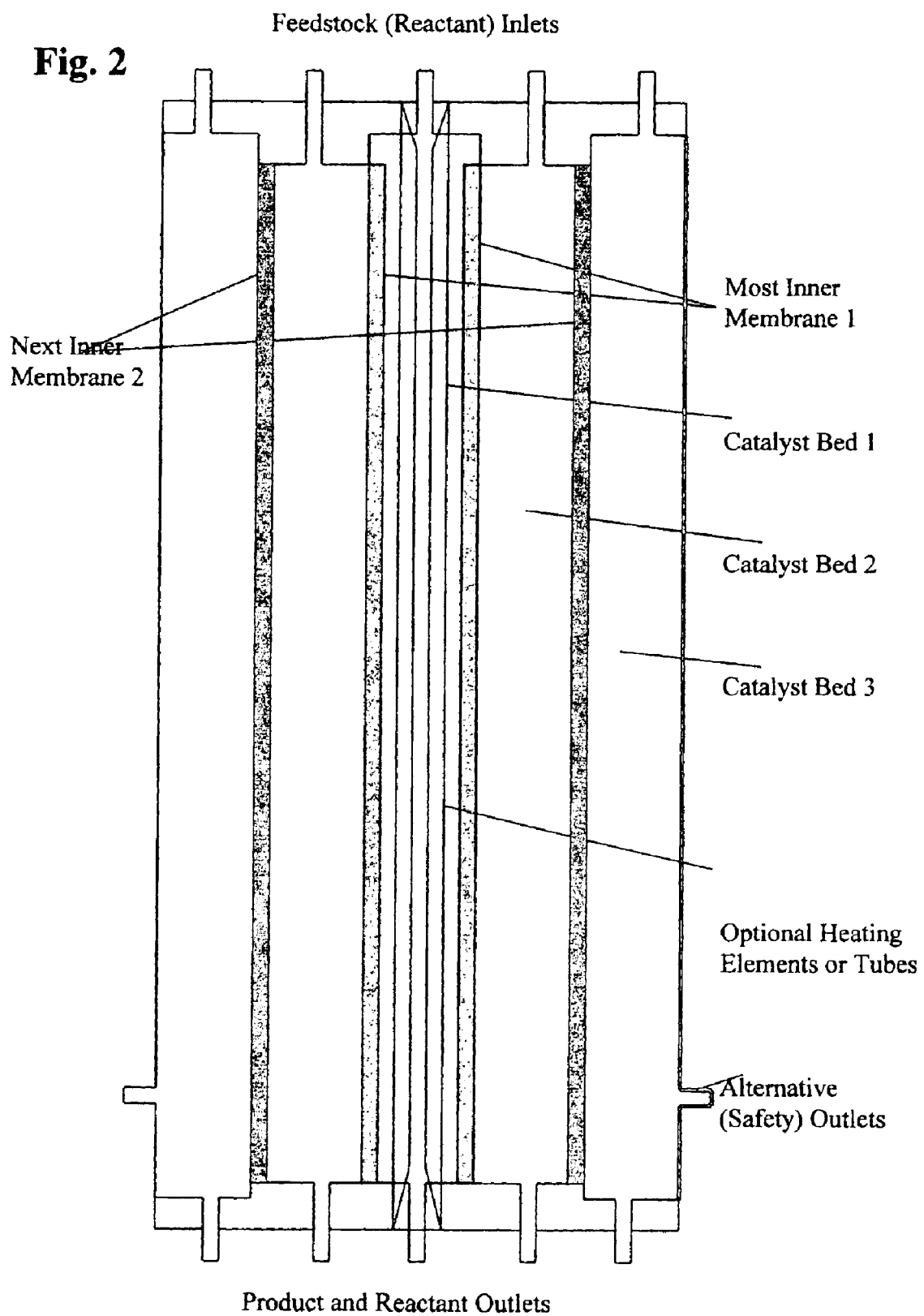
FIG. 2 shows multiple double permeable wall reactors of those described in FIG. 1, but without the external impermeable tube, which are placed symmetrically inside a larger common stainless steel tube, to create a multiple tube reactor with a common external area for collecting final permeate hydrogen.

FIG. 2, shows multiple double permeable wall reactors of those described in FIG. 1, but without the far outer impermeable tube (7), which are placed symmetrically inside a larger impermeable tube (A1), to create a multiple tube reformer with a common external area for collecting final permeate hydrogen.

Figure 3:
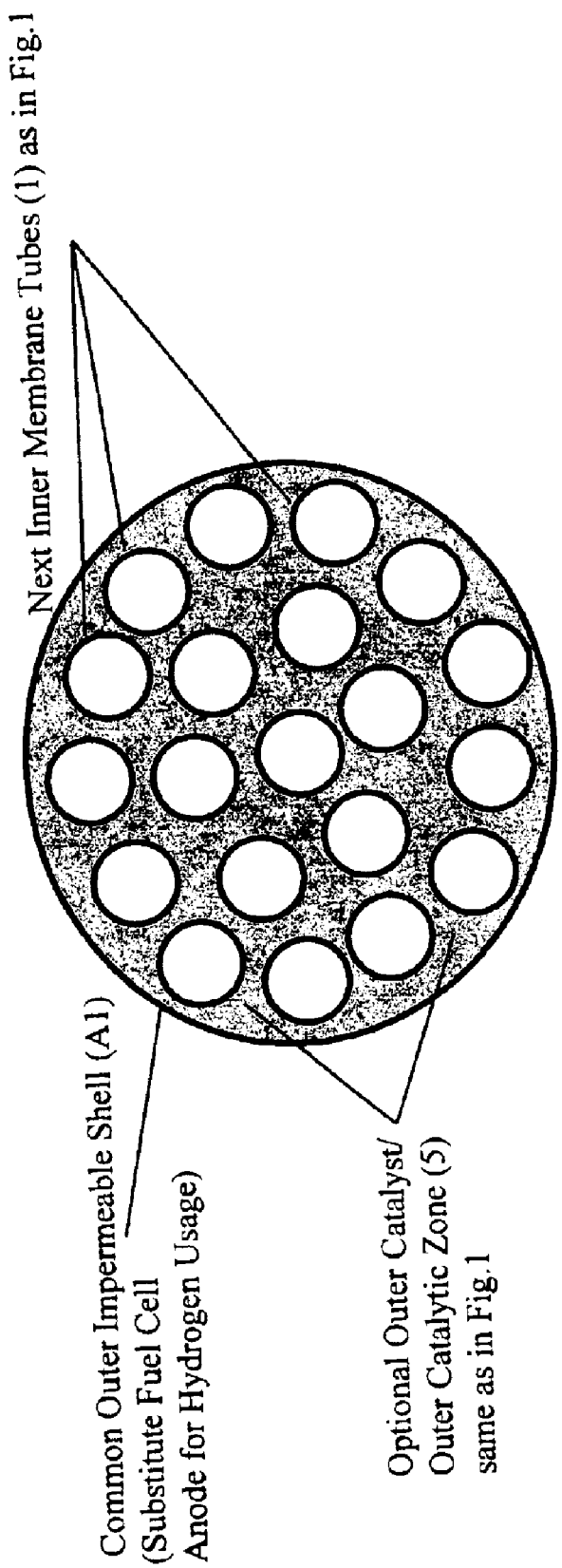
FIG. 3, shows a cross section of a concentric double permeable wall cylindrical reactor, consisting of an outer impermeable tube, a next-inner membrane tube made by metal, non-porous or porous inorganic, or carbon membrane, and a most-inner membrane tube made by metal, non-porous inorganic, carbon or organic membrane.

FIG. 3 shows another developed reformer or reactor design to be used in steam and carbon dioxide reforming of hydrocarbons, steam reforming of alcohols, water gas shift and dehydrogenation reactions. Reformer or reactor consists of a most outer impermeable tubular cylinder (shell) (1) which is hollow inside in order to nest two more concentric tubular cylinders, a next inner one (2) and finally a most-inner (3) which both are made by permeable materials. Most outer cylinder (1) is made by impermeable stainless steel or alloys, but next-inner cylinder (2) consists of metal, metal alloys, non-porous and porous inorganics, porous inorganic-metals or carbon materials such as those described in embodiment of FIG. 1.

The derived concentric cylindrical assembly has proper inlet and outlet fittings for feeding the feedstocks and discharging the post-reaction species. Proper inlet and outlet fittings are interconnected with the different sites of the cylindrical assembly. Fittings are connected to the annular space between most-outer and next-inner cylinders to deliver and collect gases flowing in this space. Additional independent fittings are connected to the annular space between the next-inner and most-inner cylinders to deliver and collect gases flowing in this space. Additional independent fittings are connected to the tubular space of the most-inner cylinder to deliver and collect gases flowing in this space. The fittings are made in such a manner so that they can seal in a leak-free manner each corresponding space, and the overall cross section of the double permeable wall cylindrical tube assembly. Before the fittings are applied and tighten, the annular space between the most outer (external) and next-inner cylinders is filled with the proper reaction catalyst in pellet or particle form to make the catalytic reaction zone (4). Proper catalyst is used for each reforming, water gas shift and dehydrogenation reactions. Catalysts used in these reactions are same with these mentioned above in description of embodiment of FIG. 1.

In steam, $CO_2$ reforming of hydrocarbons, steam reforming of alcohols, water gas shift and paraffin dehydrogenation reactions, hydrogen is removed along the next-inner lateral cylindrical metal membrane surface (2), with carbon monoxide, carbon dioxide, steam, hydrocarbons, alcohols to possibly also permeate through inner lateral membrane surface in a lesser degree than hydrogen depending on the membrane material used. An inert carrier gas such as argon, nitrogen, steam or a mixture of those gases, may flows along the permeate annulus, between tubes (2) and (3), through suitable inlet fittings, to carry the permeate components at a specific pressure value. Permeate hydrogen is further removed through permeation along the lateral surface of most-inner membrane tube (3) so that the final permeated stream contains pure hydrogen only, with pure hydrogen to be used in various applications including feed to synthesis reactors, gas turbines and engines, and fuel cells.

The most-inner membrane tube (3) is made by a metal, metal alloy, non-porous inorganic or carbon membrane which allows only hydrogen to permeate through and therefore purifies hydrogen from the permeating carbon oxides, steam and hydrocarbons, flowing in the annular zone created between the next-inner and most-inner cylindrical tubes. Membrane tubes (2) and (3) can be made with similar manufacturing techniques as those described in embodiment of FIG. 1. The most-inner membrane tube can be either empty or may contain a selective catalyst (5) which converts permeate hydrogen combined with another component flowing through the inner bore of this tube. Such a flowing (sweep) component can be an unsaturated hydrocarbon (e.g., alkenes, alkynes) for conversion to saturated hydrocarbons, after reaction with the permeate hydrogen in an exothermic reaction. Flowing (sweep) component for hydrogenation by the permeate hydrogen can be also carbon monoxide for direct production of methanol or gasoline hydrocarbons (through Fischer-Tropsch synthesis) in exothermic type reactions. Flowing (sweep) gas can be nitrogen for exothermic ammonia synthesis after combination with the permeate hydrogen. Other combination reactions with permeate hydrogen can be these for reduction of aromatic hydrocarbon, also these for saturation of unsaturated alcohols, phenols, aldehydes, ketones, acids, these for reduction of alkyl and aryl halides and these for reduction of nitroalkanes and aromatic nitro compounds to corresponding primary amines. Alternatively, pure permeate hydrogen can be used as direct feed in hydrogen based turbines and engines, fuel cells, and other power generation equipment. The heat generated by exothermic reactions in the most-inner cylindrical bore, may be transferred into the catalytic reaction zone of the outer membrane cylinder via the radial direction, thus providing part of the heat load necessary to drive the endothermic catalytic reactions in catalyst bed (4) located within the outer membrane cylinder.

Permeation of hydrogen through the first inner membrane tube, shifts the thermodynamic equilibrium conversion of reactant species to the product side and produces excess hydrogen and carbon oxide products for reforming and water gas shift reactions, and hydrogen only for paraffin dehydrogenation reactions.

Most-inner membrane tube thereby, serves as a final permeable medium for the recovery of highly pure hydrogen product for use in hydrogen utilization applications. Most-inner metal membrane tube serves also as a separation medium for hydrogen out of the annular zone between the two hollow cylindrical membrane tubes, so that partial pressure of hydrogen lowers substantially along the annular zone, and therefore continuous driving force exists for hydrogen permeation from the enclosed catalytic reaction zone (4) to the central annular zone (7), through the next inner membrane tube (2).

As an alternative to the invented design, for low operating gas reforming and dehydrogenation reaction temperatures (e.g., between 200–400° C.) and in the absence of steam as a reactant, the next-inner membrane tube (2) can be made by porous inorganic or inorganic-metal materials which are permeable to several species diffusing out of the reaction zone (4), and the most-inner membrane tube (3) can be made by organic materials which withstand high temperatures (have high glass transition temperature, Tg) and are perm-selective to both hydrogen and carbon dioxide species which flow along the central annular zone (7). The binary permeate mixture of $H_2$ and $CO_2$ can be used in applications described already in embodiment of FIG. 1.

The most-inner membrane serves also as a backup membrane medium in case the first-inner membrane develops cracks or defects and its permeability to various gases increases. In this case, the most-inner membrane will selectively separate specific gases based on the selected membrane material as described above. Moreover, operational and maintenance service for replacing old or damaged membrane and outer non-membrane tubes becomes easier with the proposed design, because each part of the reactor is interconnected with the rest and can be dissembled and assembled accordingly.

Heating of the described reformer or reactor is achieved via external heat provision (6). The external to the reformer combustion regime can be fueled by flowing waste type hydrocarbons or hydrocarbon-hydrogen mixtures mixed with oxygen or air. Unreacted hydrocarbons, carbon monoxide product, non-permeate hydrogen product, or any mixture of these post-reaction species coming out of the cylindrical reformer outlet connected with the catalyst zone (4), can be recycled as well into the external combustion-heating zone (6). Optionally, external heating of most-outer shell (1) can be provided by cylindrical type heaters or heating elements (i.e., made by ceramic, composite materials) in contact with the shell.

Figure 4:
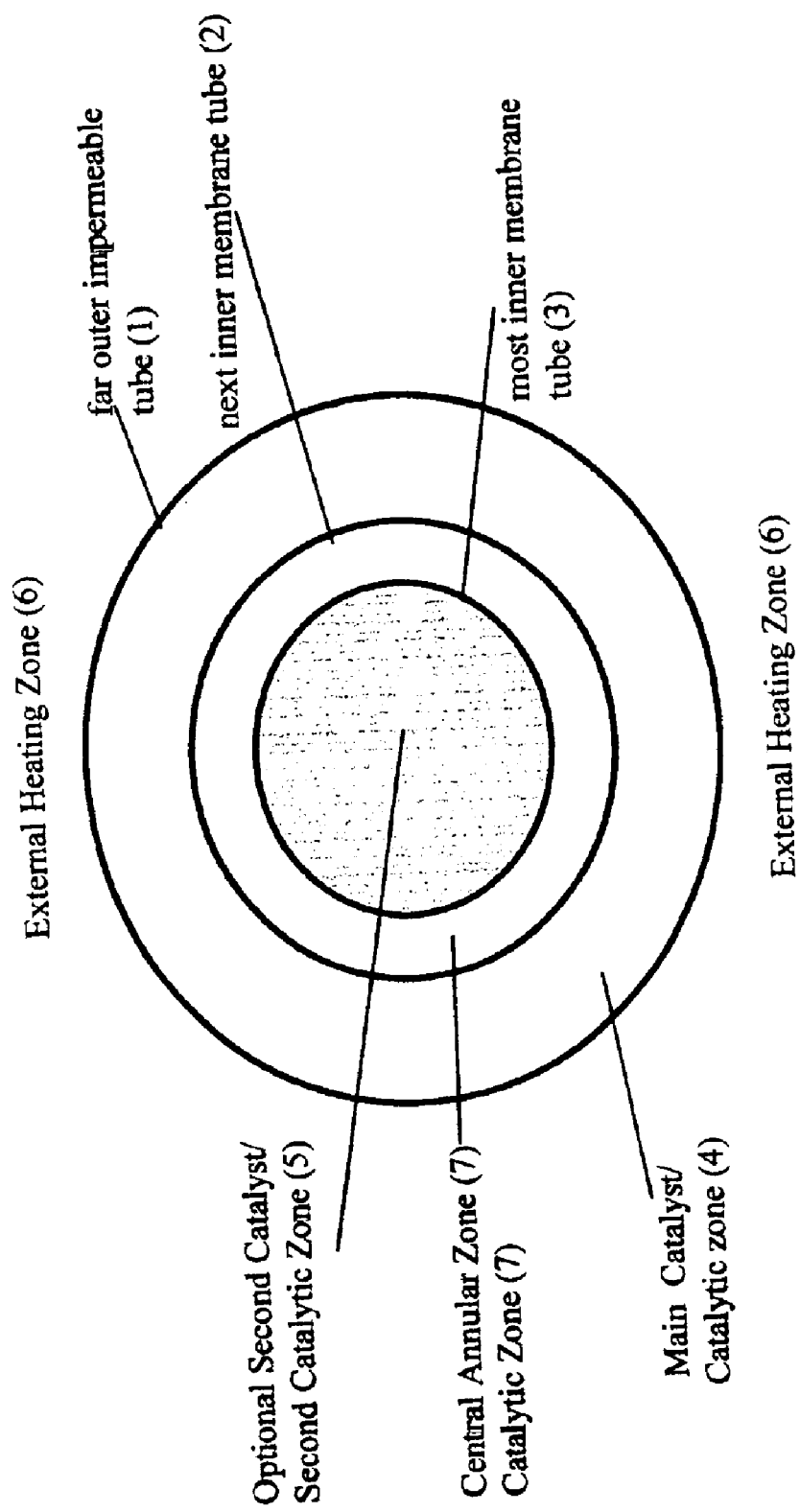
FIG. 4, shows multiple double permeable wall cylindrical reactors of those described in FIG. 3, which are placed symmetrically inside a larger stainless steel tube, to create a multiple tube reactor with a common external heating area.

FIG. 4, shows multiple double permeable wall cylinder reactors of those described in FIG. 3, which are placed symmetrically inside a larger impermeable tube (shell) (A1), to create a multiple tube reformer with a common external heating area.

Figure 5:
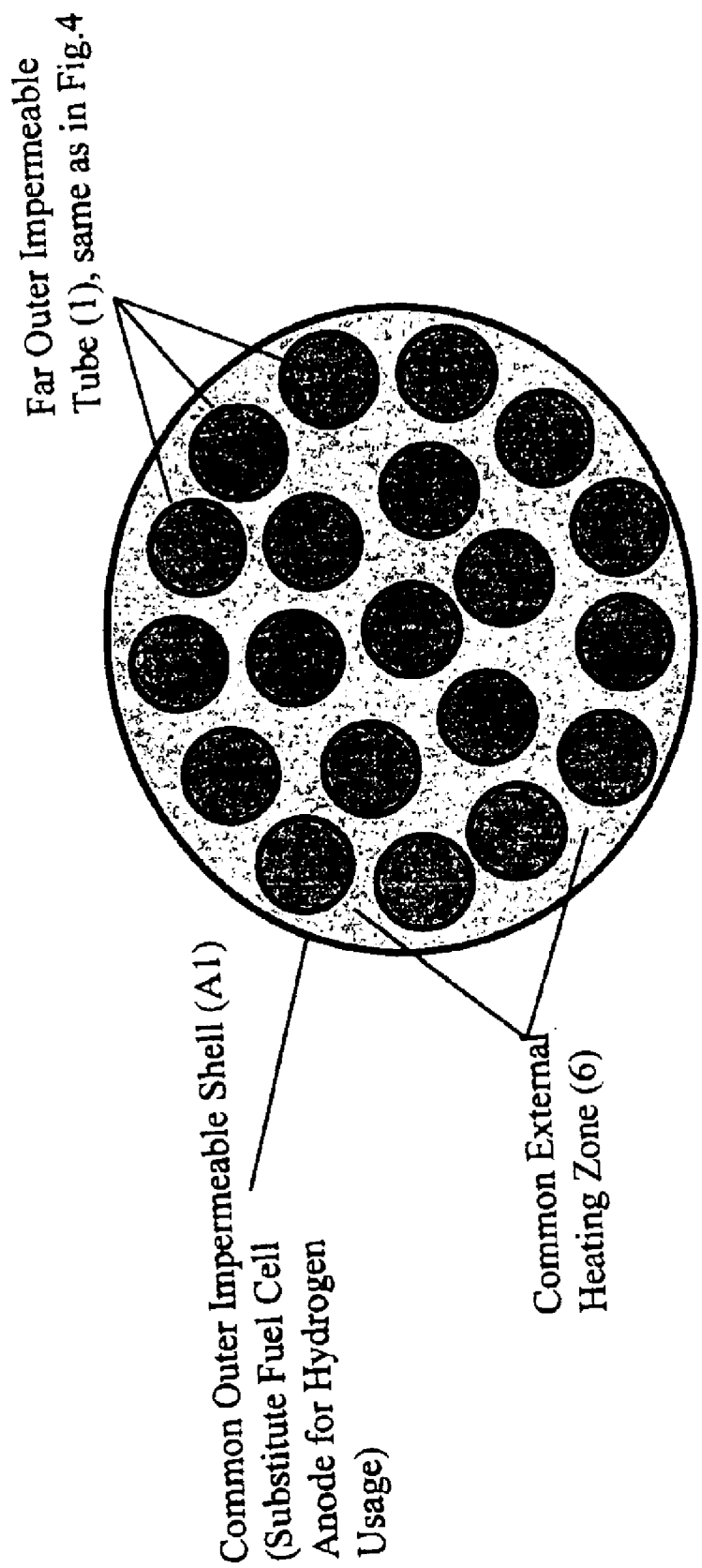
FIG. 5, shows a cross section of a multiple permeable membrane tube reactor wherein the membranes are made by an organic or composite polymer and are nested within an outer impermeable tube.

FIG. 5 shows a cross section of a reformer or dehydrogenation reactor which consists of multiple cylindrical hollow polymer membrane tubes or fibers (1) nested within an outer impermeable metal cylindrical tube (2) which also contains the catalyst (3) in particle or pellet form, for the specific reactions mentioned below.

Reacting gas feedstocks free of steam such as $CO_2$ and hydrocarbons also paraffin hydrocarbons are fed within the catalyst zone (3) through special inlet fittings and they react in the catalyst to produce hydrogen and carbon monoxide or hydrogen and olefins. Optionally, small volumetric quantities of hydrogen can be added into above feedstocks in inlet of the reactor assembly, to prevent heavy catalyst deactivation in the reactor inlet, wherein propensity for hydrocarbon cracking into carbon is high in absence of any hydrogen. The $CO_2$ (dry) reforming or dehydrogenation catalysts are the same metallic type with those described in embodiment of FIG. 1. Steam is avoided as a reactant in the reactor to avoid long term plasticization and structural damage of membrane tubes and loss of related permeability and selectivity properties.

Hydrogen product from these reactions is removed along the surface of the multiple membrane tubes (1), wherein the membranes are made by organic polymer or composite polymer membranes. Traces of carbon monoxide, carbon dioxide, product steam, olefins, and unreacted hydrocarbons may also permeate through the membrane tubes (1) in a lesser degree than hydrogen. The permeate gas mixture is continuously removed through the inner side of the membrane tubes and flows into a common impermeable metal shell which is interconnected with all the membrane tubes and sealed from the gases flowing into the catalytic reaction side (3). Optionally, a flowing component can flow along the inner membrane tube (1) to sweep and dilute the permeate gas as it flows through the tubes.

In an optional design, catalyst in form of pellets or particles (4) can be contained within the inner side of the polymer membrane tubes to carry suitable catalytic reactions (such as hydrogenations) in which one of the reacting species is permeate hydrogen and the other reaction species are contained within the flowing gas. Such a flowing (sweep) component can be an unsaturated hydrocarbon (e.g., alkenes, alkynes) for conversion to saturated hydrocarbons, after reaction with hydrogen, in an exothermic reaction. Flowing (sweep) component can also be carbon monoxide for direct production of methanol or gasoline (through Fischer-Tropsch synthesis) after combination with the permeate hydrogen, in exothermic type reactions. Flowing gas can be nitrogen for exothermic ammonia synthesis after its combination with the permeate hydrogen. Other combination reactions with permeate hydrogen over specific metallic catalysts, can be these for reduction of aromatic hydrocarbons, also these for saturation of unsaturated alcohols, phenols, aldehydes, ketones, acids, these for reduction of alkyl and aryl halides and these for reduction of nitroalkanes and aromatic nitro compounds to corresponding primary amines. Part of the heat generated by the exothermic reactions in the inner side of the tubes, may be transferred across the membranes, into the common catalytic reaction zone (3) surrounding the multiple membrane tubes, thus providing part of the bent load necessary to drive the endothermic catalytic reactions in catalyst zone (3).

Permeation of reaction products and especially hydrogen through the membrane tubes (1), shifts the thermodynamic equilibrium conversion of reactant species to the product side and produces excess hydrogen, carbon oxide, and olefins respectively within the catalytic reaction zone (3). Permeate collected hydrogen through the inner tubes (1), can be used in chemical synthesis or fuel applications as described in embodiment of FIG. 1.

As an alternative to the disclosed design, for low operating reforming and dehydrogenation temperatures (e.g., between 200–400° C.), the inner tubes (1) can be made by materials which are permselective to both hydrogen and carbon dioxide products which permeate along the surface of the tubes (1). The separated mixture of $H_2$ and $CO_3$ can be used in applications described in embodiment of FIG. 1.

The main heating of the catalyst zone (3), is achieved via external heating (5) of the impermeable most-outer reactor shell (2) through combustion of flowing waste type hydrocarbons or hydrocarbon-hydrogen mixtures mixed with oxygen or air. Unreacted hydrocarbons, carbon monoxide, non-permeate hydrogen or any mixture of these species coming out of the outlet of catalytic zone (3) can be recycled as well into the external combustion zone (5). Optionally, external heating of outer shell (2) can be provided by any type of cylindrical type heaters or heating elements (i.e., ceramic, composite).

Figure 6:
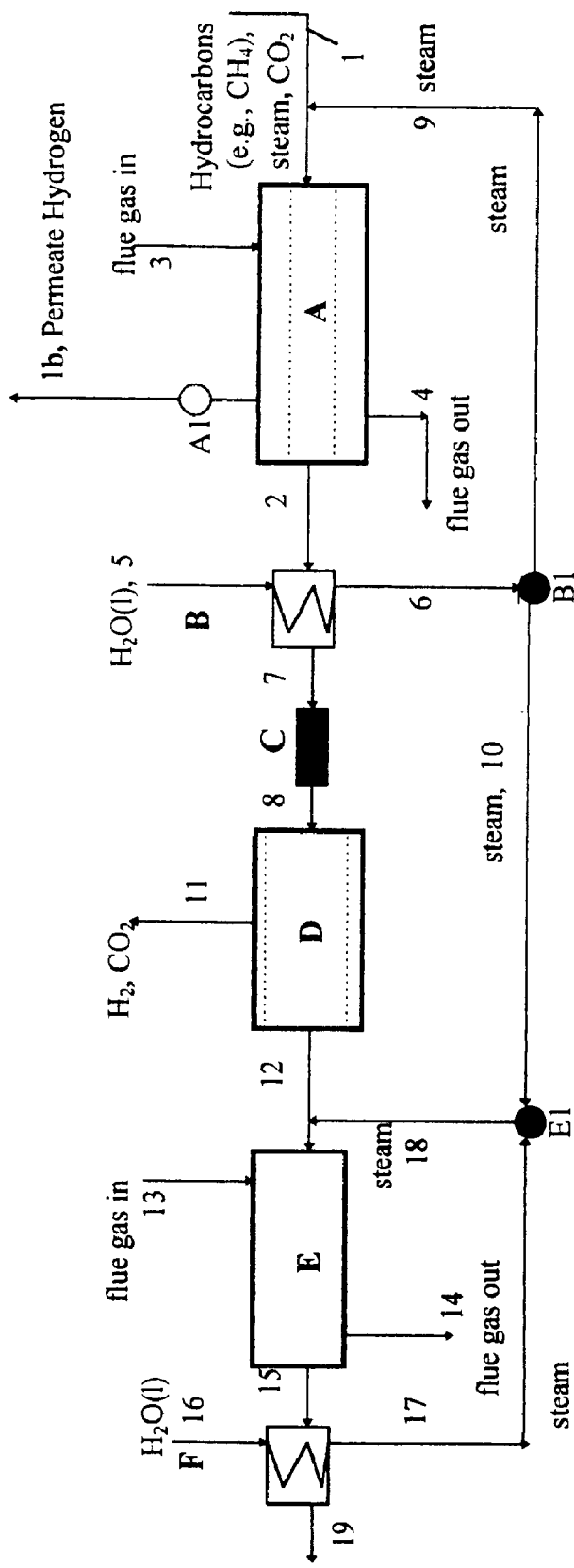
FIG. 6, shows a system of a catalytic permreactor and a consecutive permeator or optionally a system of two catalytic permreactors in series for hydrocarbon steam and $CO_2$ reforming or for hydrocarbon $CO_2$ reforming only. The reject from the permeator stream containing non-permeate hydrocarbon and CO can be optionally fed into a consecutive catalytic steam reforming reactor.

FIG. 6, depicts a system of catalytic permreactor with consecutive permeator (or optionally a permreactor) and optionally another final consecutive reactor, for conducting reforming and gas shift reactions. In FIG. 6, stream 1 contains hydrocarbon feedstocks such as methane ($CH_4$), higher alkanes (paraffins), naphtha, and natural gas, mixed with steam and $CO_2$ and introduced in catalytic permreactor A for conducting simultaneously reactions (1), (2) and (3), or mixed with $CO_2$ only for conducting reactions (2) and (3). Some hydrogen may be added into stream 1, which is usually between 1–15% of the feed volume, to depress carbon formation from hydrocarbon cracking especially in the inlet of permreactor A.

Catalytic permeable reformer A, is of any of the types described in embodiments of FIGS. 1,2,3,4, and 5 above, with $H_2$ to be separated in permeate stream 1b via valve A1, in the general case, $H_2$ and $CO_2$ combined, can be separated in permeate stream in special applications, if an organic membrane is used in permreactor A. The rejected exit stream from the permreactor may contain product CO together with unreacted steam ($H_2O(g)$), $CO_2$, and hydrocarbon, and non-permeate $H_2$. This stream becomes stream 2 and enters into heat exchanger B, where the unreacted steam is removed through condensation, and by the heat exchanging process new steam is generated in stream 6 from the water or steam of stream 5. Stream 6, can provide steam in permreactor A and reactor E through streams 9 and 10,18 respectively, in an alternative or simultaneous manner via use of valves B1,E1. The steam in 6 aquires the exchanged heat load from stream 2, the hot gas effluent of permeable reformer A, and thus its derived streams 9,10,18 can be mixed directly with streams 1 and 12 which are fed directly into reactors A and E respectively.

Steam from 6 is used via streams 10,18 and valves B1,E1 to provide the initial steam content in reformer E. Stream 7, passes through a bed of particles C (moisture adsorbent) to remove any non-condensed traces of moisture and through exit stream 8 enters into membrane permeator D. Stream 8, contains CO product, non-permeate $H_2$ product, unreacted hydrocarbon (e.g., $CH_4$) and $CO_2$ gases and has been cooled at the operating temperature of permeator D. $H_2$ or both $H_2$ and $CO_2$ are removed in permeate stream 11 of permeator D, through the permselective action of a metal, non-porous inorganic, carbon, or organic membrane respectively. Non permeating stream containing hydrocarbon (e.g., $CH_4$), CO and $CO_2$ or hydrocarbon and CO respectively, depending on the type of membrane used in permeator D, exits from permeator D, through stream 12 as reject stream. Stream 12 enters into reformer E, for conducting simultaneously reforming and water shift reactions selected from the group of reactions (1), (2) and (3), and be converted to final $H_2$, CO, $CO_2$ or $H_2$ and $CO_2$ only products, depending on the feed composition of stream 12 in reformer E. Steam in reformer E is provided via stream 18. Unreacted steam is removed from exit stream 15 by passing this stream through heat exchanger F. Steam is generated from water or steam of stream 16 and via streams 17,18 and valve E1, the generated steam is fed into inlet of reformer E. Exit stream 19 contains $H_2$, CO, $CO_2$ or $H_2$, $CO_2$ products and traces of unreacted hydrocarbons, depending on the operating conditions, that is the temperature, pressure, space velocity and feed composition of streams 12 and 18, or reformer E. Reformer E can be replaced by a permeable reformer E similar to permeable reformer A, wherein $H_2$ is separated in permeate and the reject exit stream 19 consists of CO and $CO_2$ or $CO_2$ only.

Reformers A and E are endothermic and flue gas streams 3,4 and 13,14 respectively are used to provide the necessary heat content to drive parallel reactions (1), (2) and (3) to completion. The two reformers can operate at same or different temperature and pressure conditions.

If conversion is high in permeable reformer A under certain operating conditions, the product in stream 2 is mainly CO and $H_2$ which can be used directly as synthesis gas in methanol synthesis via the direct exothermic reaction: $CO+2H_2=CH_3OH$, also in Fischer-Tropsch type reactions for production of gasoline type hydrocarbons, and as fuel in gas turbines and engines and solid oxide fuel cells for power generation.

If the overall process consists of two reformers and the intermediate permeator, and the final product is a $H_2$ and $CO_2$ mixture in exit stream 19, it can be used separately or it can be mixed with stream 11 to make a combined $H_2$ and $CO_2$ stream. This combined $H_2$, $CO_2$ mixture can be used for direct methanol synthesis via the exothermic reaction: $3H_2+CO_2=CH_3OH(g)+H_2O(g)$. Also, the $H_2$, $CO_2$ mixture can be used as direct feed in molten carbonate fuel cells for electricity generation via the overall electrochemical reaction:

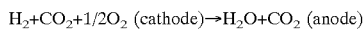

$H_2+CO_2+1/2O_2$ (cathode)→$H_2O+CO_2$ (anode)

Alternatively, $CO_2$ can be condensed cryogenically from the binary mixture and pure hydrogen can be produced. Final $H_2$ product can be used for chemical synthesis or as direct feed in fuel cells and gas turbines and engines for power generation applications (e.g., transportation, stationary). Applicable hydrogen driven fuel cells for utilizing the pure separated hydrogen from the process, include proton exchange membrane (PEM), solid oxide (SOFC), molten carbonate (MCFC), alkaline (AFC), phosphoric acid (PAFC) and modifications and combinations of these fuel cells.

Generated hydrogen product from the process can be combined with an unsaturated hydrocarbon (e.g., alkenes, alkynes) for conversion to saturated hydrocarbons in an exothermic type reaction. Also, with carbon monoxide for direct production of methanol (as described above) or gasoline (through Fischer-Tropsch synthesis) in exothermic type reactions. Hydrogen can be also combined with nitrogen for exothermic ammonia synthesis. Other combination (synthesis) reactions with permeate hydrogen can be these for reduction of aromatic hydrocarbons, also these for saturation of unsaturated alcohols, phenols, aldehydes, ketones, acids, these for reduction of alkyl and aryl halides and these for reduction of nitroalkanes and aromatic nitro compounds to corresponding primary amines.

The described process is able to overcome the thermodynamic equilibrium limitations of hydrocarbon ($CH_4$) and $CO_2$ reactant conversion, through the removal of $H_2$ only, or of $H_2$ and $CO_2$ gases in membrane permreactor A and permeator D. The calorific value of the obtained $H_2$, CO product in permreactor A, is higher than this of the reactant hydrocarbon (e.g., $CH_4$), $CO_2$ and steam and the endothermic heat of reaction is stored in the products which can be subsequently used as fuels or in chemical synthesis.

Assuming 100% conversion of reactions (1) and (2) and reaction (3) in equilibrium in permreactor A, 2 mol of $CH_4$ (with heat of combustion: 425.6 kcal), 1 mol of $CO_2$ (with no heat of combustion), and 1 mol of $H_2O(g)$ (with no heat of combustion), produce 3 mol of CO (with heat of combustion: 202.8 kcal) and 5 mol of $H_2$ (with heat of combustion: 341.5 kcal). These values are at 25° C. This corresponds to about 28% increase in calorific value for the product. Endothermic heat can be provided in reformers A and E through the combustion of flue or waste gases or unreacted recycled hydrocarbons coming out of the exit of reaction zone of reformers A and E as also described in FIGS. 1 and 3 above.

In an alternative design, permeator D is replaced by a catalytic permreactor D wherein the water gas shift reaction occurs if stream 8 is rich in product CO. In such case permreactor D is made by metal, non-porous inorganic, or carbon membranes to separate only hydrogen in permeate. Exit reject stream 12 from permreactor D contains product $CO_2$ and unreacted steam and can be recycled in the first reforming permreactor or used in downstream applications either as a mixture or as pure $CO_2$ after condensation of the steam.

Figure 7:
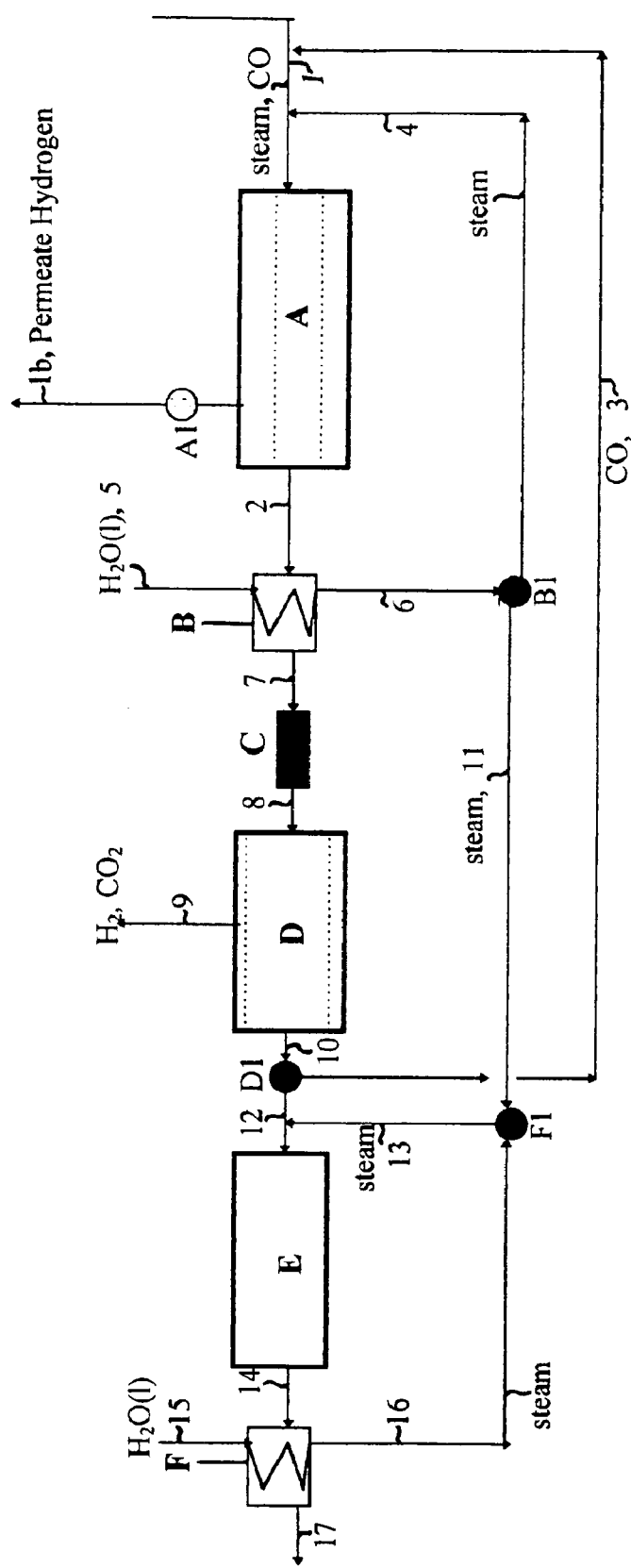
FIG. 7, shows a similar process as in FIG. 6 in which the initial feedstock consists only of CO and steam, to undergo water gas shift reaction only in the first catalytic permreactor. The reject from the permeator, CO stream, can be recycled into the initial permreactor or optionally fed into a consecutive water gas shift reactor.

FIG. 7, describes a similar embodiment with the one described in FIG. 6, but feed stream 1 contains carbon monoxide (CO) only, mixed with steam, and introduced in catalytic permreactor A which is filled with catalyst particles to conduct the water gas shift reaction only.

Catalytic permeable water gas shift reactor A, is of any of the types described in embodiments of FIGS. 1,2,3,4, and 5 above, with $H_2$ to be separated in permeate stream 1b via valve A1, in the general case. $H_2$ and $CO_2$ combined, can be separated in permeate stream for special applications, if an organic membrane is used in permreactor A. The rejected exit stream from the permreactor contains product CO together with unreacted steam ($H_2O(g)$) and non-permeate $H_2$. This stream becomes stream 2 and enters into heat exchanger B, where the unreacted steam is removed through condensation, and by the heat exchanging process new steam is generated in stream 6 from the water or steam of stream 5. Stream 6, can provide steam is permreactor A and reactor E through streams 4 and 11,13 respectively, in an alternative or simultaneous manner via use of valves B1,F1. The steam in 6 acquires the exchanged heat load from stream 2, the hot gas effluent of permeable reactor A, and thus its derived streams 4,11,13 can be mixed directly with streams 1 and 12 which are fed directly into reactors A and E respectively.

Steam from 6 is used via streams 11,13 and valve F1 to provide initial steam in reactor E. Stream 7 passes through a bed of particles (moisture adsorbent) C to remove any non-condensed traces of moisture and through exit stream 8 enters into membrane permeator D. Stream 8 contains non-permeate product $H_2$, product $CO_2$ and unreacted CO gases and has been cooled at the temperature of permeator D. $H_2$ and $CO_2$ are removed in permeate stream 9 through permselective action of membrane in permeator D. Non permeating CO exits from permeator through stream 10 which can be called a reject stream. Stream 10 can be recycled via valve D1 and stream 3 into the first permeable shift reactor A for contiuous shift reaction and conversion to $H_2$ and $CO_2$ products. Alternatively, by use of same valve D1, stream 10 becomes 12 which enters into reactor E for additional shift reaction (2), and conversion to final $H_2$, $CO_2$ products. Steam in E is provided via stream 13. Unreacted steam is removed from exit stream 14 by passing this stream through heat exchanger F. New steam is generated from water or steam of stream 15 and via streams 16,13 and valve F1 is fed into inlet of reactor E. Exit stream 17 contains $H_2$, $CO_2$ products and traces of unreacted CO depending on the operating conditions, that is the temperature, pressure and feed composition of streams 12 and 13, of reactor E.

Shift reactors A and E are exothermic and no heat input is necessary as with the previous endothermic reformers described in previous embodiments. Stream 1 needs to be preheated in temperature of permeable reactor A before entering into reactor. Using the heat content of streams 2 and 14 exiting from the reactors to provide the necessary heat content in the feed streams 4 and 13 entering into the reactors, the entire process operates in an autothermic way with no additional heat input necessary. The two shift reactors can operate at same or different temperature and pressure conditions.

Exit stream 17 can be used separately or it can be mixed with stream 9 to make a combined $H_2$ and $CO_2$ stream to be used for chemical synthesis or as fuel in applications similar to the ones mentioned above for the reforming reactors. Pure $H_2$ from the process can be recovered after the $CO_2$ condensation and removal. Pure hydrogen from the process can be used as fuel or in chemical synthesis applications, as described in embodiment of FIG. 6 above.

The described shift process is able to overcome the equilibrium CO reactant conversion limitations, through removal of $H_2$ in permreactor A and intermediate removal of $H_2$ and $CO_2$ products in permeator D. Thus, the process increases CO conversion and $H_2$, $CO_2$ yields above those obtained in conventional water gas shift reaction separation systems for production of $H_2$ and $CO_2$. By use of the two heat exchangers each shift reactor operates in an autothermic way with no need of additional heat load in the system except for the initial preheating of stream 1 to start-up operation in permreactor A.

Figure 8:
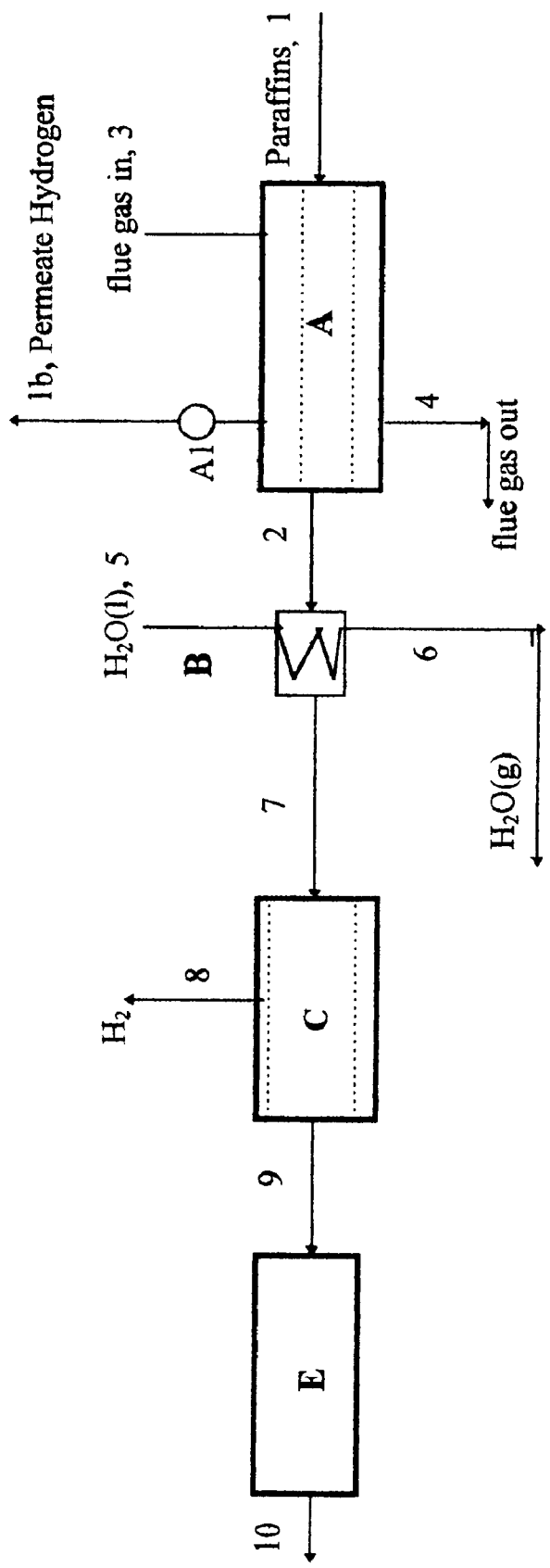
FIG. 8, shows a permreactor-permeator or reactor-permeator system applied for catalytic dehydrogenation of $C_1$–$C_4$ or higher alkane hydrocarbons; the reject from the membrane permeator olefinic stream can be used for polyolefin production.

FIG. 8 is an embodiment of a system of catalytic permreactor with consecutive permeator for conducting paraffin (alkane) dehydrogenation reactions. In FIG. 8, stream 1 contains hydrocarbon feedstocks such as ethane, propane, n-butane, i-butane, naphtha, or liquid alkanes such as pentane, hexane, heptane. Liquid alkanes are vaporized by preheating before fed into catalytic permeable dehydrogenator A. Some hydrogen may be added into stream 1, which is usually between 1–15% of the feed volume, to depress carbon formation in the catalyst from hydrocarbon cracking especially in the inlet of permreactor A.

Catalytic permeable dehydrogenator A, is of any of the types described in embodiments of FIGS. 1,2,3,4, and 5 above, with $H_2$ to be separated in permeate stream 1b via valve A1. The rejected exit stream from permreactor A contains unreacted paraffins, product olefins, and non-permeate hydrogen. This stream becomes stream 2 and optionally passes through heat exchanger B, where by the heat exchanging process steam is generated in stream 6 from the water of steam of stream 5 to be used in steam requiring applications.

Stream 7, enters into membrane permeator C. $H_2$ is removed in permeate stream 8 of permeator C, through the permselective action of a metal, non-porous inorganic, carbon or organic membrane. Non permeating stream containing hydrocarbons (product olefins and traces of unreacted paraffins) exits from permeator C, through stream 9 as reject stream. Stream 9 has composition dependent on the paraffin conversion in permreactor A and the hydrogen separation efficiency in permeator C. By optimizing these two parameters, pure olefins can be produced in stream 9, to be used as direct feed in polyolefin reactors E for polyolefin production (i.e., polyethylene, polypropylene) exiting from stream 10. Olefins from stream 9 are also used as direct feed in synthesis reactors, such as ethylene for ethylene oxide and ethylene glycol production, propylene for propylene oxide and propylene glycol production, isobutylene for oxygenated gasoline production. Produced pure hydrogen from the described process can be used into same fuel and synthesis applications as described in embodiment of FIGS. 1 and 3. Paraffin dehydrogenation reactions are endothermic, and reactor A receives heat from flue gas streams 3,4 to drive dehydrogenation reactions (4) to completion.

The described process is able to overcome the thermodynamic equilibrium limitations of paraffin hydrocarbon conversion met in conventional reactors, through the removal of product $H_2$ in membrane permreactor A and permreactor C. Endothermic heat can be provided in dehydrogenator A through the combustion of flue or waste hydrocarbons or unreacted recycled hydrocarbons from the reaction zone of reactor A as also described in embodiments of FIGS. 1,3 and 5 above.

Permeable dehydrogenator A can be substituted by non-permeable (e.g., non-porous stainless steel wall) dehydrogenator A. Valve A1 and stream 1b are eliminated and all post-reaction gases exit from stream 2. Permeator C still operates in same function as described above.

Figure 9:
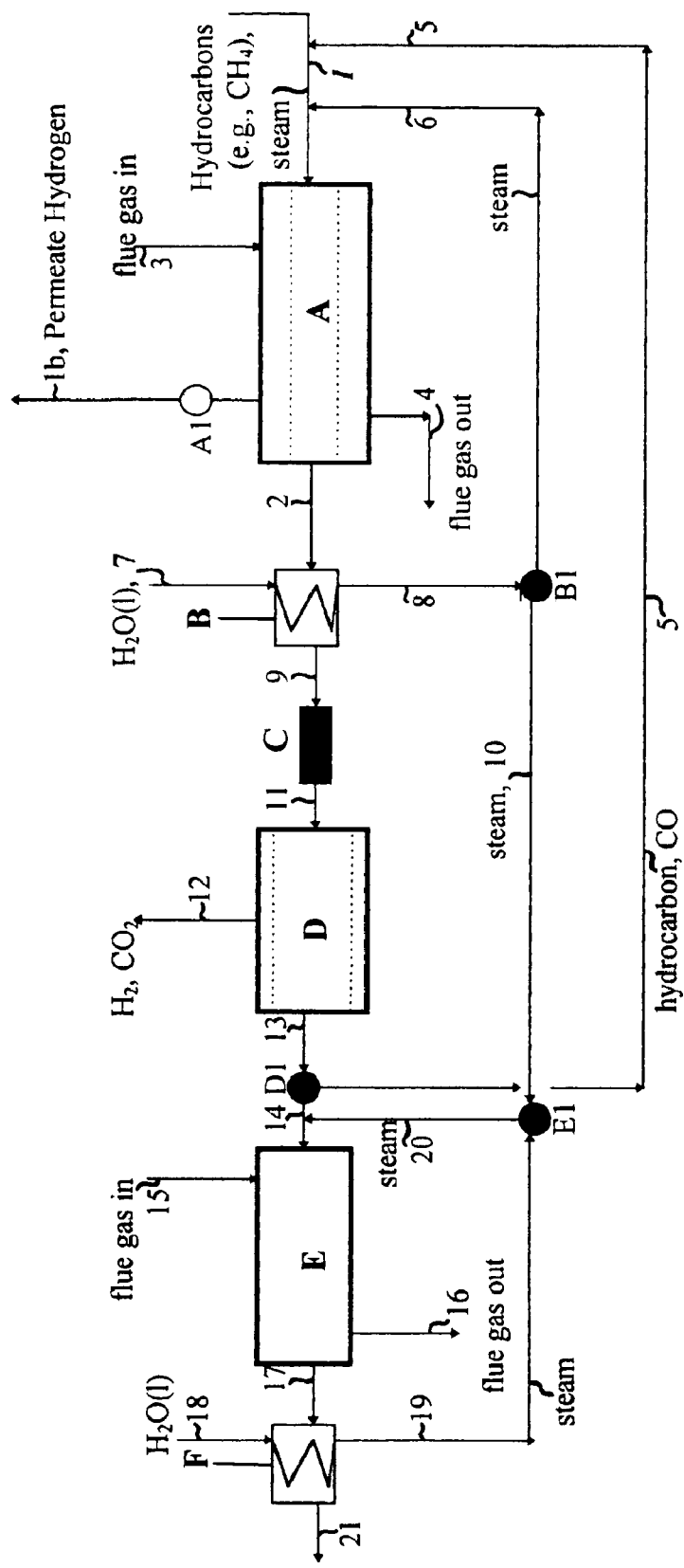
FIG. 9, shows a catalytic permreactor-permeator system for the hydrocarbon steam reforming reaction. The reject from the membrane permeator hydrocarbon and CO stream can be recycled into the initial reformer or fed into a consecutive steam reforming reactor.

FIG. 9, is an embodiment which is related with these described in FIGS. 6 and 7, but with stream 1 to contain hydrocarbon feedstocks such as methane or higher alkanes such as naphtha and natural gas, also alcohol feedstocks such as methanol, ethanol, propanol, butanol mixed with steam only and introduced in catalytic permreactor A which is filled with catalyst particles to conduct the methane steam reforming reaction (1) and the simultaneously occurring water gas shift reaction (3). Some hydrogen may be added into stream 1, which is usually between 1–15% of the feed volume, to depress carbon formation from hydrocarbon cracking especially in the inlet of the reactor A.

Catalytic permeable reformer A, is of any of the types described in embodiments of FIGS. 1,2,3,4, and 5 above, with $H_2$ to be separated in permeate stream 1b via valve A1, in the general case. $H_2$ and $CO_2$ combined, can be separated in permeate stream in special applications, if an organic membrane is used in permreactor A. The rejected exit stream from the permreactor may contain product $CO_2$, CO, unreacted steam ($H_2O(g)$) and hydrocarbon, and non-permeate $H_2$. This stream becomes stream 2 and enters into heat exchanger B, where the unreacted steam is removed through condensation, and by the heat exchanging process new steam is generated in stream 8 from the water or steam of stream 7. Stream 8, can provide steam in permreactor A and reactor E through streams 6 and 10,20 respectively, in an alternative or simultaneous manner via use of valves B1,E1. The steam in 8 acquires the exchanged heat load from stream 2, the hot gas effluent from permeable reformer A, and thus its derived streams 6,10,20 can be mixed directly with streams 1 and 14 which are fed directly into reactors A and E respectively.

Steam from 8 is used via streams 10,20 and valve E1 to provide initial steam in reformer E. Stream 9 passes through a bed of particles (moisture adsorbent) C to remove any non-condensed traces of moisture and through exit stream 11 enters into membrane permeator D. Stream 11 has been cooled in temperature of permeator D and contains CO, $CO_2$, unreacted hydrocarbon, non-permeate $H_2$ gas species.

$H_2$ or both $H_2$ and $CO_2$ are removed in permeate stream 12 of permeator D, through the permselective action of a metal, non-porous inorganic, carbon or organic membrane respectively. Non permeating stream containing hydrocarbon (e.g., $CH_4$), CO and $CO_2$ or hydrocarbon and CO respectively, depending on the type of membrane used in permeator D, exits from permeator D, through stream 13 as reject stream. In case wherein stream 13 contains hydrocarbon and CO it can be recycled via valve D1 and stream 5 into first permeable reformer A for continuous reforming and conversion to main $H_2$ and $CO_2$ products. Alternatively, by use of valve D1, stream 13 becomes stream 14 which enters into steam reformer E for additional reforming and shift reactions, via reactions (1) and (3) and additional conversion to $H_2$ and $CO_2$ products. In case wherein stream 13 contains hydrocarbon, CO and $CO_2$, using valve D1, stream 13 becomes stream 14 which enters into modified steam and $CO_2$ reformer E for additional reforming and shift reactions, via reactions (1), (2) and (3) and conversion to $H_2$, CO, $CO_2$ products. Reformer E, can be replaced by a permeable reformer E similar to permeable reformer A, wherein $H_2$ is separated in permeate and the reject exit stream 17 consists of product CO and $CO_2$ or $CO_2$ only.

Reformers A and E are endothermic and flue gas streams 3,4 and 15,16 respectively are used to provide the necessary heat content to drive parallel reactions (1), (2) and (3) to completion. The two reformers can operate at same or different reaction temperature and pressure conditions. If conversion is high in permeable steam reformer A under certain operating conditions, the product in stream 2 is mainly $CO_2$ and non-permeate $H_2$ which can be used directly in applications described already in embodiment of FIGS. 1 and 3.

If the overall process consists of two reformers and the intermediate permeator, and the final product is $H_2$ and $CO_2$ in exit stream 21, this product can be used separately or it can be mixed with stream 12 to make a combined $H_2$ and $CO_2$ stream to be used in similar applications. Alternatively, $CO_2$ can be condensed cryogenically from the binary mixture and pure hydrogen product is produced. Final $H_2$ product can be used for chemical synthesis or as direct feed in fuel cells and gas turbines and engines for power generation applications (e.g., transportation, stationary), same to these described in embodiment of FIG. 6.

The described process is able to overcome the thermodynamic equilibrium limitations of hydrocarbon ($CH_4$) and steam reactant conversion, through the removal of $H_2$ product only, or of the combined $H_2$ and $CO_2$ products in membrane permreactor A and permeator D. The calorific value of the obtained $H_2$, $CO_2$ product in permreactor A, is higher than this of the reactant hydrocarbon (e.g., $CH_4$) and steam mixture, because the provided endothermic heat of reaction is stored in the products and can be subsequently released by using products as fuels or in chemical synthesis.

Assuming 100% conversion of reactions (1) and (3), 1 mol of $CH_4$ (with heat of combustion: 212.8 kcal) and 2 mol of $H_2O(g)$ (with no heat of combustion) generate 1 mol of $CO_2$ (with no heat of combustion) and 4 mol of $H_2$ (with heat of combustion: 273.3 kcal). These values are at 25° C. This corresponds to about 28% increase in calorific value for the product gases. By providing external heat through flue or waste gas input in the reformers and with the described two heat exchangers in place, the energy requirement of the one reactor-one permeator or two reactor-one permeator cascades is fulfilled and the processes operates in a thermally independent manner providing for an energy efficient design. Endothermic heat can be provided in reformers A and E through the combustion of flue or waste gases or unreacted recycled hydrocarbons from the reaction zone of reformers A and E, as also described in FIGS. 1,3,5 above.

Figure 10:
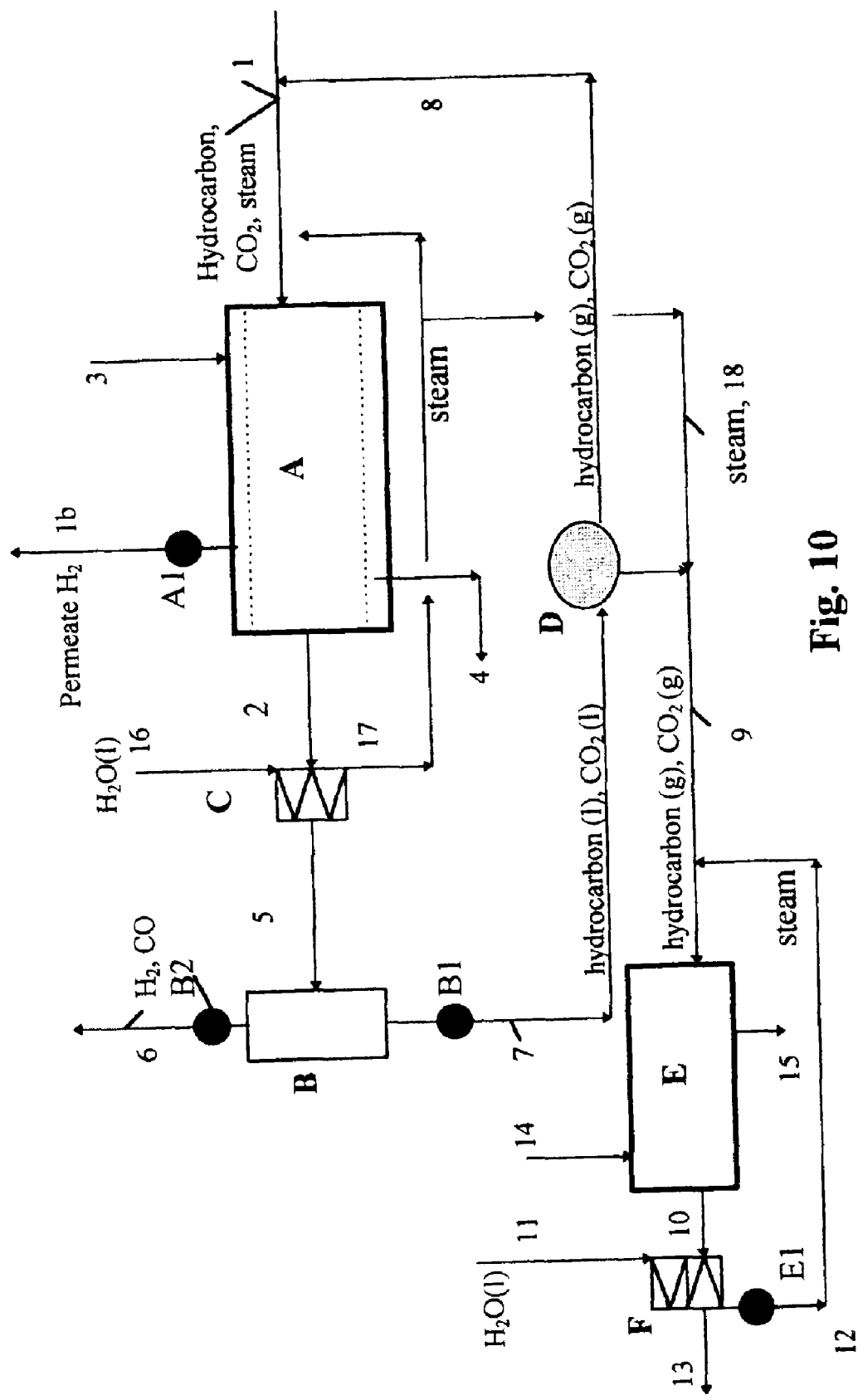
FIG. 10, shows a system of a catalytic permreactor or impermeable reactor with a consecutive cryogenic separator for hydrocarbon steam and $CO_2$ reforming or for hydrocarbon $CO_2$ reforming only. The one stream separated from the cryogenic separator, containing hydrocarbon, $CO_2$ and steam can be alternatively fed into the inlet of the initial reforming reactor.

FIG. 10, is an embodiment of a steam and $CO_2$ hydrocarbon reforming process which includes a permeable reformer or a non-permeable reformer followed by a cryogenic separator for separation of certain post-reaction gases exiting from the reject exit of the reformer. In FIG. 10, stream 1 is introduced into catalytic permreactor hydrogen, containing hydrocarbon feedstocks such as methane ($CH_4$) mixed with steam and $CO_2$ for conducting simultaneously reactions (1), (2) and (3), or mixed with $CO_2$ only for conducting reactions (2) and (3). Some hydrogen may be added into stream 1, which is usually between 1–15% of the feed volume, to depress carbon formation from methane cracking especially in the inlet of permreactor A.

Catalytic permeable reformer A, is of any of the types described in embodiments of FIGS. 1,2,3,4, and 5 above, with $H_2$ to be separated from the reformer, and exit in permeate stream 1b via valve A1. The rejected exit stream from the permreactor contains product CO together with unreacted steam ($H_2O(g)$), $CO_2$, and hydrocarbon, and non-permeate $H_2$. This stream becomes stream 2 and enters into a steam condenser C wherein the unreacted steam is condensed and by the heat exchanging process new steam is generated in steam 17 from the water or steam of stream 16. Steam through stream 17 is recycled into stream 1 in inlet of reformer A. Stream 5 free of steam, exits from condenser C and enters into cryogenic separator B, which operates at a temperature lower than the boiling temperature of carbon dioxide and hydrocarbons so that these compounds are separated as liquids and collected in the bottom of the separator (operating cryogenic temperature of the separator is a negative number which has larger absolute value than the absolute value of any of the boiling points of the liquified components above). However, operating cryogenic temperature of separator is higher than the boiling points of carbon monoxide and hydrogen so that these compounds remain in the gas phase and exit from the separator as a gas mixture (operating cryogenic temperature of the separator is a negative number which has smaller absolute value than the absolute value of the boiling points of both hydrogen and carbon monoxide). Liquified components exit via stream 7 through valve B1. Gas phase hydrogen and carbon monoxide exit as stream 6 via valve B2. Liquified stream 7 can be recycled into the feed stream of reformer A (stream 1) via stream 8 after evaporation in evaporator D. Alternatively, stream 8 can be further processed in another reforming reactor by becoming stream 9 which enters into reformer E, for additional steam and $CO_2$ reforming of any remaining hydrocarbons via reactions (1), (2) and (3). Optional, steam in reformer E is provided via stream 18. Stream 10 exiting the reformer can optionally condense the containing unreacted steam by passing through the heat exchanger F. Inlet stream 11 contains water which becomes steam in stream 12 after passing through F. Steam in stream 12 can optionally fed into reformer E via valve E1. Stream 13 exiting the heat exchanger F is dry, and contains $H_2$ and CO as main products with traces of unreacted hydrocarbons and $CO_2$ depending on the operating temperature and pressure of the reformer E and the composition of feed streams 10 and 12.

Recovered $H_2$ and CO in stream 13 can be either used separately or optionally be combined with stream 6 from the separator to make one stream to be used as fuel or in chemical synthesis. Direct application of the produced $H_2$ and CO mixture is in methanol synthesis via the direct exothermic reaction: $CO+2H_2=CH_3OH$, also in Fischer-Tropsch type reactions for production of gasoline type hydrocarbons, and as fuel in gas turbines and engines and solid oxide fuel cells for power generation. Similarly, $H_2$ recovered in stream 5, can be used as fuel or in chemical synthesis, as described in embodiment of FIG. 6. The described process is able to overcome the thermodynamic equilibrium limitations of hydrocarbon (e.g., $CH_4$), steam and $CO_2$ reactant conversion, through the removal of $H_2$ and $H_2$ and CO gases in membrane permreactor A and cryogenic separator B respectively. Endothermic heat in reformers A and E is provided through gas streams 3,4 and 14,15 respectively. Streams 3, 14 can be fed by a bypass stream of exit stream 2, as also described in embodiments of FIGS. 1,3,5. The reformer A can be optionally substituted by a non-permeable reformer A, wherein stream 1b and valve A1 are eliminated and all product $H_2$ is included in post-reaction mixture entering through stream 2 into cryogenic separator B.

Figure 11:
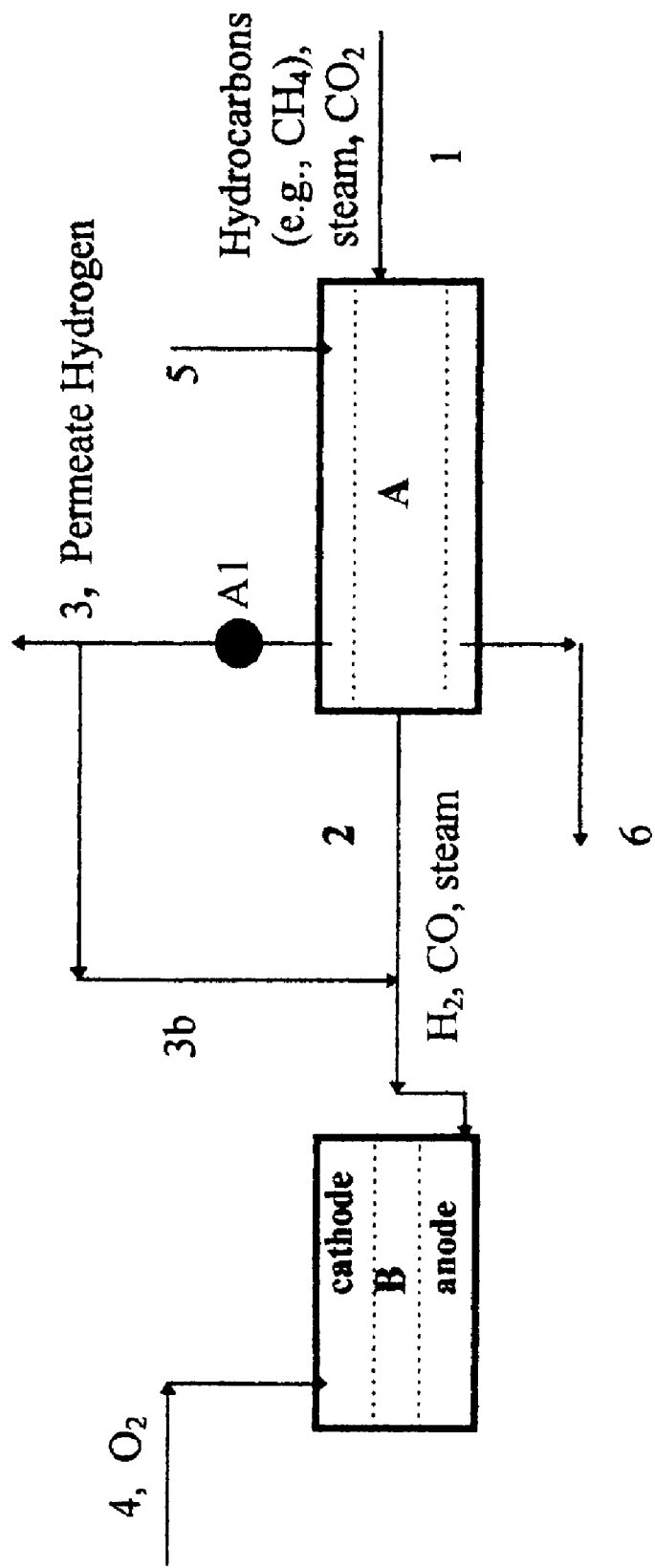
FIG. 11, shows a system of a catalytic permreactor or impermeable reactor for hydrocarbon steam and $CO_2$ reforming or hydrocarbon $CO_2$ reforming only with complete conversion of hydrocarbon and $CO_2$ gases to $H_2$ and CO, which product mixture is fed directly into an SOFC (solid oxide fuel cell) unit for electric current generation.

FIG. 11, is a modified embodiment of the process described in FIG. 6. It applies to complete conversion of hydrocarbon (i.e., CH$_4$) and CO$_2$ reactants of stream 1, within the permeable reformer A, to H$_2$ and CO products. The occurring reactions are (1),(2),(3) or (2),(3) only. Catalytic permeable reformer A, is of any of the types described in embodiments of FIGS. 1,2,3,4, and 5 above, with H$_2$ to be separated in permeate stream 3 via valve A1. Exiting from the permreactor, stream 2, containing only CO and non-permeating H$_2$, or CO, non-permeating H$_2$, and traces of unreacted steam, enters into a solid oxide fuel cell (SOFC) unit B. Stream 2 is directed in the anode of the solid oxide cell, and consists the fuel constituent of the fuel cell. O$_2$ in stream 4, is directed in the cathode of the fuel cell and consists the oxidant, for the well known electrochemical reaction conducted within the cell with electric current generation:

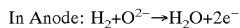

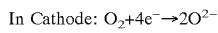

Optionally, part of hydrogen from permeate stream 3, can be fed into stream 2, via bypass stream 3b, to adjust the composition of H$_2$ in stream 2 to that required to feed the fuel cell B. The reformer A can be optionally substituted by a non-permeable reformer A, wherein all product H$_2$ is included in exit stream 2. Flue gas streams 5 and 6, are used to provide the endothermic heat content into the reformer A. Stream 5 can be fed by a bypass stream of exit stream 2, as also described in embodiments of FIGS. 1,3,5. Permeable reformer A can be substituted by a non-permeable (e.g., stainless steel) reformer A. Valve A1 and streams 3, 3b are eliminated and all post-reaction gases exit from stream 2. Fuel cell B still operates in same function as described above.

Figure 12:
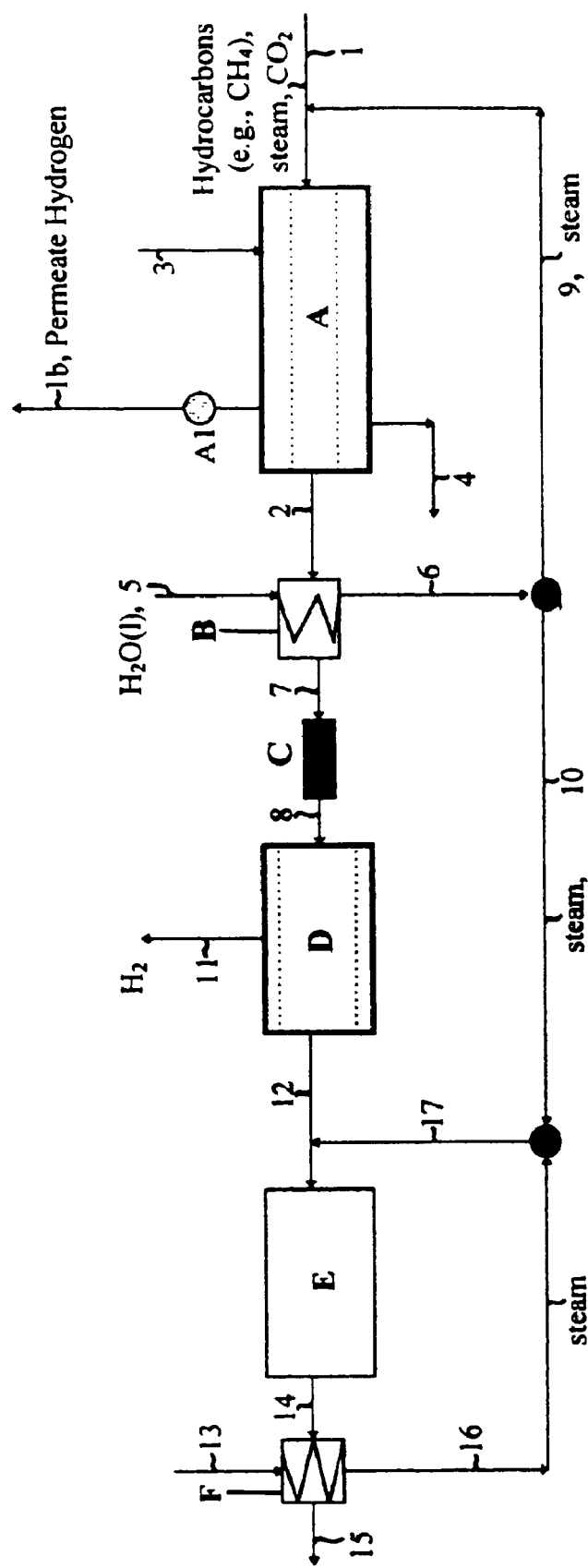
FIG. 12, shows a system of a catalytic permreactor or impermeable reactor followed by a membrane permeator for hydrocarbon steam and $CO_2$ reforming or hydrocarbon $CO_2$ reforming only with complete conversion of hydrocarbon and $CO_2$ feedstocks to $H_2$ and CO which product mixture enters into the permeator which separates $H_2$ via permeation from CO.

FIG. 12. is an embodiment which describes a modified operation of the process described in FIG. 6. It applies to complete conversion of hydrocarbon (i.e., CH$_4$) and CO$_2$ reactants of stream 1, within the permeable reformer A, to H$_2$ and CO products. The occurring reactions within the reformer are (1),(2),(3) or (2),(3) only. Catalytic permeable reformer A, is of any of the types described in embodiments of FIGS. 1,2,3,4, and 5 above, with H$_2$ to be separated in permeate stream 1b via valve A1. Exiting from the permreactor, stream 2, containing only CO and non-permeating H$_2$, or CO, non-permeating H$_2$, and traces of unreacted steam, passes through heat exchanger B and moisture adsorbent C to remove unreacted steam, and enters into permeator D as a dry stream. Hydrogen is separated in stream 11 from carbon monoxide, rejected by the membrane, and exiting via stream 12. Carbon monoxide, via stream 12, can be optionally fed into a consecutive water gas shift reactor E for conversion to final H$_2$ and CO$_2$ products. A heat exchanger F is used in exit of the water gas shift reactor E, to remove any unreacted steam, with final stream 15 to contain only H$_2$ and CO$_2$. The reformer A can be optionally substituted by a non-permeable reformer A, wherein all reaction product H$_2$ is included in exit stream 2 and stream 1b, valve A1 are eliminated.

Hydrogen from stream 11 can be used in applications mentioned already in embodiment described in FIG. 6 and FIG. 9. Similarly CO from stream 12, or H$_2$ and CO$_2$ from stream 15 can be used in aforementioned applications described already in embodiments of FIGS. 6,9 and 10.

Figure 13:
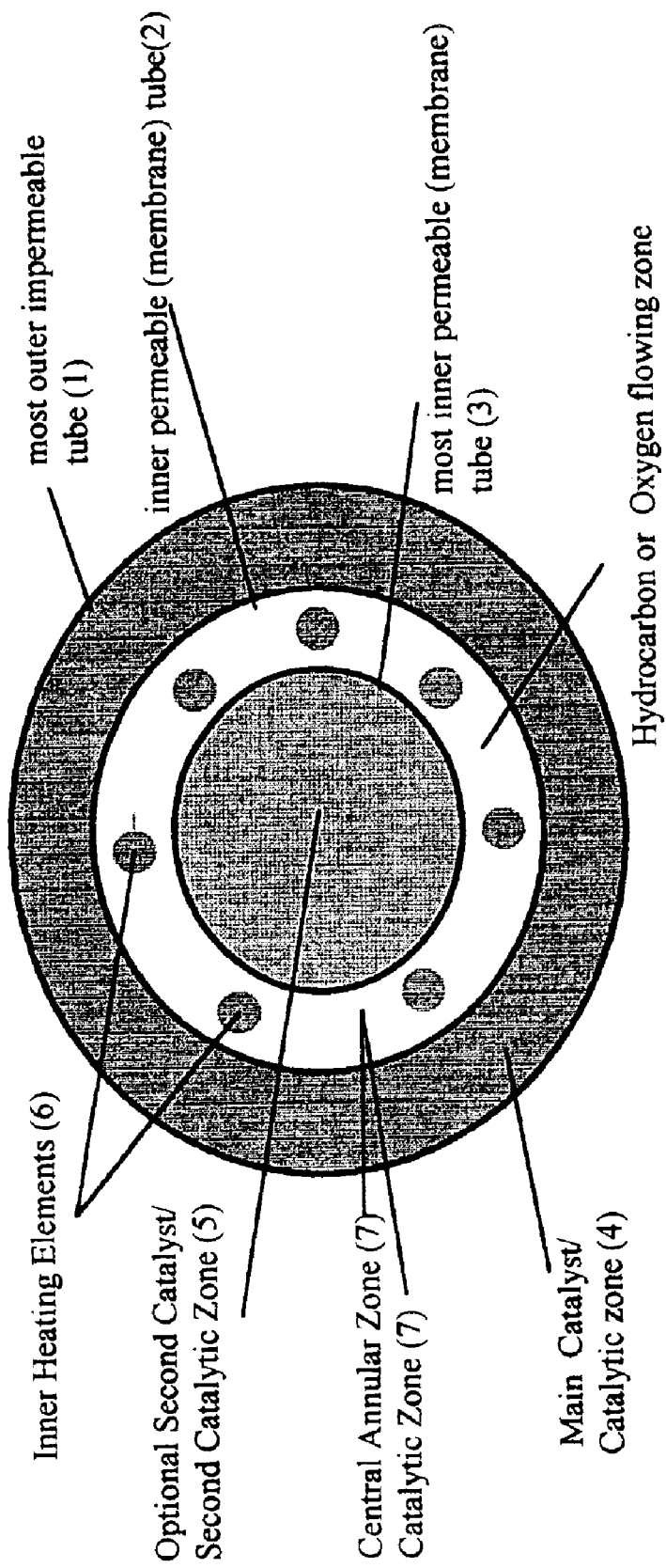
FIG. 13, shows a system of a catalytic permreactor for hydrocarbon, steam and $CO_2$ reforming or hydrocarbon $CO_2$ reforming only with a consecutive methanol synthesis reactor from hydrogen, CO and $CO_2$ or hydrogen and CO only followed by a methanol steam reforming reactor for production of $H_2$ and $CO_2$. The system of reactors includes recycling streams of $H_2$ and $CO_2$ for increasing the overall process efficacy.

FIG. 13. is an embodiment of a modified process of the process described in FIG. 6. It pertains to methanol production from the products of the reforming reaction occurring in reactor A, and the subsequent utilization of methanol in a methanol-steam reforming reactor. The process describes the complete conversion of hydrocarbon (i.e., CH$_4$) and CO$_2$ reactants, in stream 1, within the permeable reformer A, to H$_2$ and CO products. The occurring reactions are (1),(2),(3) or (2),(3) only. Catalytic permeable reformer A, is of any of the types described in embodiments of FIGS. 1,2,3,4, and 5 above, with H$_2$ to be separated in permeate stream 1b via valve A1. Exiting from the permreactor, stream 2, containing only CO and non-permeating H$_2$, or CO, non-permeating H$_2$, and traces of unreacted steam, passes through heat exchanger B and moisture adsorbent C to remove unreacted steam and yield an all dry stream of H$_2$ and CO. Stream 8, of H$_2$ and CO (synthesis gas) enters into the methanol synthesis reactor D, wherein methanol is produced via the following exothermic reaction: CO+2H$_2$=CH$_3$OH, $\Delta H_{298}$=−128.2 kJ/mol (13.1). Reactor D, is a three phase slurry type reactor or a catalytic plug flow reactor with methanol to be produced in gas or liquid phase depending on the temperature, pressure and feed composition in the reactor and the type of catalyst used. Zinc, copper and chromium oxide catalysts are well known to convert synthesis gas to methanol. Methanol from stream 9 is fed to a methanol driven fuel cell for electric current generation. Optionally, stream 9 containing methanol enters into steam reforming reactor E for continuous catalytic methanol-steam reforming reaction in similar type membranes. The reforming reaction in reactor E is as follows: CH$_3$OH+H$_2$O=3H$_2$+CO$_2$, $\Delta H^{0}_{298}$=49.5 kJ/mol (13.2). Exiting from the reactor E, gaseous stream 11, condenses unreacted steam and methanol in heat exchanger F, and the exit product gas through stream 14 is H$_2$ and CO$_2$. Steam in reactor E is provided through streams 6,10,13,15 which is generated by the heat exchanging process in heat exchangers B and F.

Pure H$_2$ and CO$_2$ mixture from exit stream 14, can be used as feed in molten carbonate fuel cells or in alternative methanol synthesis via the opposite reaction of methanol steam reforming, listed above. Optionally, bypass stream 16 can be fed into stream 8 to add CO$_2$ and H$_2$ into the synthesis gas mixture fed into reactor D, to adjust its composition for increasing methanol production efficiency in the catalyst in reactor D via the reverse (13.2) reaction. Optionally also, stream 1c, which is a bypass stream of stream 1b and contains pure hydrogen, can be recycled into stream 8 via stream 16, for adjusting the hydrogen composition in this stream where necessary, to increase the efficiency of methanol synthesis in reactor D. Streams 15 and 1c merge into stream 16 via valve D1.

Hydrogen in stream 14 can be used as a mixture with CO$_2$ or as pure H$_2$ after the CO$_2$ condensation and removal. Produced hydrogen from steams 1b and 14, can be used in applications mentioned already in embodiments described in FIG. 6 and FIG. 9. The H$_2$ and CO$_2$ mixture of stream 14 can be used in synthesis or fuel applications mentioned already in same embodiments. Reformers A and E are endothermic and flue gas streams 3.4 and 18.9 respectively are used to provide the necessary heat content to drive parallel reactions (1), (2), (3) and (13.2) respectively to completion. Streams 3 and 18 can be fed by a bypass stream of stream 2. Optionally, reformer A can be a non-permeable reformer with only one post-reaction outlet (exit), this of stream 2, which delivers all products and unreacted reactants into the heat exchanger B and next into reactor D.

What is claimed is:

1. A process for conducting catalytic reforming of hydrocarbons and alcohols with steam and carbon dioxide for the production of pure hydrogen which includes the use of:

a far outer impermeable hollow tubular cylinder nesting two more concentric permeable tubular cylinders, a next inner and a most inner one, having the most inner permeable cylinder nested within the next inner permeable cylinder thus defining three different annular zones for the catalytic reforming reactions of said components, including next inner membrane and most inner membrane, with the most inner permeable cylinder filled with a reforming catalyst in pellet or particle from which comes in contact with the reactant hydrocarbons, alcohols, steam and carbon dioxide, and including gas heating tubes located along the most inner axis for heating the catalyst to the temperature of said reforming reaction, with the hydrogen product coming from the reforming reactions between hydrocarbons or alcohols with steam and carbon dioxide continuously removed via permeation along the most inner membrane, wherein most inner membrane is made from an inorganic or composite material, with the remaining reaction species partially permeating as well via the most inner membrane, with the permeated species diluted by an inert carrier gas flowing along the next inner annular zone, with hydrogen only continuously removed via permeation along the next inner membrane and continuously withdrawn as well out of the most inner catalytic zone causing for the continuous equilibrium shift of said catalytic reforming reactions evolving within this zone, with next inner membrane made from a metal or non-porous inorganic material permeable only to hydrogen, and with pure hydrogen permeating through the next inner membrane and withdrawn along the far outer cylindrical zone.

2. The process of claim 1 wherein the most inner membrane is made from one or more materials selected from the group consisting of alumina, silica, titania, yttria, zirconia, and the next inner membrane made from one or more materials selected from the group consisting of aluminum carbide and nitride, silicon carbide and nitride, titanium carbide and nitride, zirconium carbide and nitride, tantalum carbide and nitride, palladium, silver, copper, zinc, tantalum, vanadium, tungsten.

3. The process of claim 1 wherein the feed hydrocarbon or alcohol is a single component or a mixture of components selected from the group consisting of methane, ethane, propane, n-butane, i-butane, methanol, ethanol, propanol, butanol, naphtha, gasoline, natural gas, coal gas containing methane, landfill gas containing methane, flue gas containing methane, biomass and sewage gas containing methane.

4. The process of claim 1 wherein the combined feed hydrocarbon and carbon dioxide gas mixture is selected from the group consisting of a $CH_4$ and $CO_2$ mixture, acidic natural gas containing $CH_4$ and $CO_2$, coal gas containing $CH_4$ and $CO_2$ landfill gas containing $CH_4$ and $CO_2$, biomass and sewage gas containing $CH_4$ and $CO_2$, flue and waste gas mixture containing $CH_4$ and $CO_2$.

5. The process of claim 1 wherein the reject exit stream from the most inner and next inner annular zones is subject to a condensation step which removes steam from the said reject exit stream, and subsequently passed through a membrane permeator wherein the hydrogen and carbon dioxide gases are separated by permeation via a polymer or composite membrane and the non permeated hydrocarbons, alcohols, and carbon monoxide exit from the non-permeate side of the permeator as a reject stream.

6. The process of claim 5, wherein the reject stream from the permeator containing each one or a mixture of unreacted hydrocarbons, alcohols, and carbon monoxide is fed in a consecutive steam reforming reaction zone for additional production of hydrogen and carbon dioxide gas products.

7. The process of claim 5, wherein the reject stream from the permeator containing each one or a mixture of unreacted hydrocarbons, alcohols, and carbon monoxide is recycled into the initial catalytic most inner reforming zone for continuous reforming reaction.

8. The process of claim 1, wherein the reject exit streams from the most inner and next inner annular zones have the contained steam required by condensation and subsequently passed through a cryogenic separator, wherein the contained in stream hydrogen and carbon monoxide are separated as gases, while the hydrocarbons, alcohols, and carbon dioxide are separated as condensed liquids and after heating are recycled back into the inlet of the preceding most inner catalytic reforming zone, wherein the separated hydrogen and carbon monoxide product mixture coming from the cryogenic separator is used in following listed consecutive applications; for fuel gas in solid oxide and molten carbonate fuel cells, for gas in gas turbines and gas engines.

9. The process of claim 8 wherein the reactant hydrocarbon is methane and the reactant alcohol is methanol.

10. The process of claim 8, wherein a part of the separated liquefied hydrocarbons, alcohols, and carbon dioxide components from the cryogenic separator are mixed with steam and fed into a subsequent reforming reaction zone for additional production of hydrogen and carbon monoxide.

11. The process of claim 1, wherein the reject exit stream consists of hydrogen, carbon monoxide and unreacted steam and enters as a fuel gas feed into a solid oxide or molten carbonate fuel cell for continuous generation of electricity, wherein part or all of the permeate hydrogen coming out of the preceding membrane zone is fed as well in the fuel cell anode inlet providing for the supplementary hydrogen fuel feed.

12. The process of claim 11 wherein the flue hot gas emitted by the fuel cell is used for at least partial heating of the preceding most inner catalytic reaction zone.

13. The process of claim 16 wherein the flue hot gas emitted by the fuel cell comprises of steam and carbon dioxide and is recycled in the inlet of the preceding most inner catalytic zone for use as a reactant in the reforming reaction.

14. The process of claim 1 wherein the permeate hydrogen from the membrane zone is used as fuel feed in a consecutive fuel cell for continuous generation of electricity, wherein the fuel cell is one of the listed types: solid oxide, molten carbonate, proton exchange membrane, phosphoric acid, alkaline.

15. The process of claim 14 wherein the flue hot gas emitted by the fuel cell is used for at least partial heating of the preceding most inner catalytic zone.

16. The process of claim 14 wherein the flue hot gas, emitted by the solid oxide and molten carbonate fuel cell, which contains steam and carbon dioxide, is recycled in the inlet of the preceding most inner catalytic zone for use as a reactant in the reforming reaction.

17. The process of claim 14, wherein the fuel cell is of a cylindrical shape and its fuel anode encloses the cylindrical permeator by receiving and consuming directly the permeate hydrogen gas as fuel, wherein the flue hot gas emitted by the fuel cell is used for at least partial heating of the enclosed most inner catalytic reforming zone.

18. The process of claim 1, wherein the reject exit stream rich in hydrogen and carbon monoxide after steam condensation is used as fuel feed in a gas engine or g gas turbine for continuous generation of electricity, wherein part or all of the permeate hydrogen coming out of the preceding membrane zone is fed as well in the engine or turbine providing for the supplementary hydrogen fuel.

19. A process for conducting catalytic reforming of hydrocarbons and alcohols with steam and carbon dioxide for production of pure hydrogen which includes the use of:

a far outer impermeable hollow tubular cylinder nesting two more concentric permeable tubular cylinders, a next-inner and a most-inner one, having the most inner permeable cylinder nested within the next inner permeable cylinder thus defining three different annular zones for the catalytic reforming reactions of said components, including next inner membrane and most inner membrane, with the annular space between the far outer and next-inner cylinders filled with a reforming catalyst in pellet or particle form which comes in contact with the reactant hydrocarbons, alcohols, steam and carbon dioxide, with the hydrogen product coming from the reforming reactions between hydrocarbons or alcohols with steam and carbon dioxide continuously removed via permeation along the next-inner membrane wherein next-inner membrane is made from an inorganic or composite material, with the remaining reaction species partially permeating as well via the next inner membrane, with the permeated species diluted by an inert carrier gas flowing along the next inner annular zone, with hydrogen only continuously removed via permeation along the most inner membrane causing for the continuous withdrawal of hydrogen out of the far outer catalytic zone and for the continuous equilibrium shift of said catalytic reforming reactions evolving within this zone, with said most inner membrane made from a metal or non-porous inorganic material permeable only to hydrogen, and with the permeated pure hydrogen withdrawn along the most inner cylindrical zone.

20. The process of claim 19 wherein the next inner membrane is made from one or more materials selected from the group consisting of alumina, silica, titania, zirconia, yttria, and the most inner membrane made from one or more materials selected from the group consisting of aluminum carbide and nitride, silicon carbide and nitride, titanium carbide and nitride, zironcium carbide and nitride, tantalum carbide and nitride, palladium, silver copper, zinc, tantalum, vanadium, tungsten.

21. The process of claim 19 wherein the feed hydrocarbon or alcohol is a single component or a mixture of components selected from the group consisting of methane, ethane, propane, n-butane, i-butane, methanol, ethanol, propanol, butanol, naphtha, gasoline, natural gas, coal gas containing methane, landfill gas containing methane, flue or waste gas containing methane, biomass and sewage gas containing methane.

22. The process of claim 19 wherein the combined feed hydrocarbon and carbon dioxide gas mixture is selected from the group consisting of a $CH_4$ and $CO_2$ mixture, acidic natural gas containing $CH_4$ and $CO_2$, coal gas containing $CH_4$ and $CO_2$, landfill gas containing $CH_4$ and $CO_2$, biomass and sewage gas containing $CH_4$ and $CO_2$, flue and waste gas mixture containing $CH_4$ and $CO_2$.

23. The process of claim 19, wherein the reject exit streams from the far outer and next inner annular zones have the contained steam removed by condensation, and subsequently passed through a membrane permeator, wherein the contained in stream hydrogen and carbon dioxide are separated by permeation via a polymer or composite membrane and the non permeated hydrocarbons, alcohols, and carbon monoxide exit from the non-permeate side of the permeator is a reject stream, wherein the separated hydrogen and carbon dioxide product mixture is used as a combined fuel-oxidant feed in a molten carbonic fact cell.

24. The process of claim 23, wherein the reject stream from the permeator containing each one or a mixture of unreacted hydrocarbons, alcohols, and carbon monoxide is fed in a consecutive steam reforming reaction zone for additional production of hydrogen and carbon dioxide gas products.

25. The process of claim 23, wherein the reject stream from the permeator containing each one or a mixture of unreacted hydrocarbons, alcohols, and carbon monoxide is recycled into the preceding catalytic far outer reforming zone for continuous reforming reaction.

26. The process of claim 19, wherein the reject exit streams from the far outer and next inner annular zones have the contained steam removed by condensation and subsequently passed through a cryogenic separator wherein the contained in stream hydrogen and carbon monoxide are separated as gases while the hydrocarbons, alcohols, and carbon dioxide are separated as condensed liquids and after heating are recycled back into the inlet of the preceding for outer catalytic reforming zone, wherein the separated hydrogen and carbon monoxide product mixture containing from the cryogenic separator is used in the following listed consecutive applications: for fuel gas in solid oxide and molten carbonate fuel cells, for fuel gas in gas turbines and gas engines.

27. The process of claim 26 wherein the reactant hydrocarbon is methane and the reactant alcohol is methanol.

28. The process of claim 26, wherein part of the separated liquefied hydrocarbons, alcohols, and carbon dioxide components from the cryogenic separator is mixed with steam and fed into a consecutive reforming reaction zone for additional production of hydrogen and carbon monoxide which is used in the following listed consecutive applications: for fuel gas in solid oxide and molten carbonate fuel cells, for fuel gas in gas turbines and gas engines.

29. The process of claim 19, wherein the reject exit stream consists of hydrogen, carbon monoxide, and unreacted steam and enters as a fuel gas feed into a solid oxide or molten carbonate fuel cell for continuous generation of electricity, wherein part or all of the permeate hydrogen coming out of the preceding membrane zone is fed as well in the fuel cell anode inlet providing for supplementary hydrogen fuel feed.

30. The process of claim 29 wherein the flue hot gas emitted by the fuel cell is used for at least partial heating of the preceding far outer catalytic reaction zone.

31. The process of claim 29 wherein the flue hot gas emitted by the fuel cell containing steam and carbon dioxide, is recycled in the inlet of the preceding far outer catalytic zone for use as a reactant in the reforming reaction.

32. The process of claim 19 wherein the permeate hydrogen from the membrane zone is used as fuel feed in a consecutive fuel cell for continuous generation of electricity, wherein the fuel cell is one of the listed types: solid oxide, molten carbonate, proton exchange membrane, phosphoric acid alkaline.

33. The process of claim 32 wherein the flue hot gas emitted by the fuel cell is used for at least partial heating of the preceding far outer catalytic zone.

34. The process of claim 32 wherein the flue hot gas containing steam and carbon dioxide, emitted by the solid oxide and molten carbonate fuel cell, is recycled in the inlet of the preceding far outer catalytic zone for use as a reactant in the reforming reaction.

35. The process of claim 32, wherein the fuel cell is of cylindrical shape and its fuel anode encloses the cylindrical permeator by receiving and consuming directly the permeate hydrogen gas as fuel, wherein the flue hot gas emitted by the fuel cell is used for at least partial heating of the enclosed far outer catalytic reforming zone.

36. The process of claim 32, wherein the reject exit stream rich in hydrogen and carbon monoxide after steam condensation is used as fuel feed in a gas engine or a gas turbine for continuous generation of electricity, wherein part or all of the permeate hydrogen coming out of the preceding membrane zone is fed as well in the engine or turbine providing for the supplementary hydrogen fuel.

37. A process for conducting catalytic hydrocarbon reforming with carbon dioxide, for production of pure hydrogen and carbon dioxide which includes the use of:

a far outer impermeable hollow tubular cylinder nesting two more concentric permeable tubular cylinders, a next-inner and a most-inner one, having the most inner permeable cylinder nested within the next inner permeable cylinder thus defining three different annular zones for the catalytic reforming reactions of said components including next inner membrane and most inner membrane, with the annular space between the far outer and next-inner cylinders filled with a reforming catalyst in pellet or particle form which comes in contact with the reactant hydrocarbons and carbon dioxide, with hydrogen and carbon dioxide coming from said reforming reactions continuously removed via permeation along the next-inner membrane wherein next-inner membrane is made from an inorganic or composite material, with the remaining reaction species partially permeating as well via the next inner membrane and with the permeated species diluted by an inert carrier gas flowing along the next inner annular zone, with said hydrogen and carbon dioxide species continuously removed via permeation along the most inner membrane, causing for the continuous withdrawal of hydrogen out of the far outer catalytic zone and for the continuous equilibrium shift of said catalytic reforming reactions evolving within this zone, with said most inner membrane made from a polymer or inorganic material which is permeable to both hydrogen and carbon dioxide species, with the permeated binary hydrogen-carbon dioxide mixture withdrawn by flowing along the most inner cylindrical zone.

38. The process of claim 37 wherein the next inner membrane is made from one or more materials selected from the group consisting of alumina, silica, titania, zirconia, yttria, and the most inner membrane made from one or more materials selected from the group consisting of alumina, silica, titania, zirconia, yttria, polyimides, polycarbonates, polybenziimidazoles, polyphospazenes, polysulfones.

39. The process of claim 37 wherein the feed hydrocarbon or alcohol is a single component or a mixture of components selected from the group consisting of methane, ethane, propane, n-butane, i-butane, methanol, ethanol, propanol, butanol, naphtha, gasoline, natural gas, coal gas containing methane, landfill gas containing methane, flue and waste gas containing methane, biomass and sewage gas containing methane.

40. The process of claim 37 wherein the combined feed hydrocarbon and carbon dioxide gas mixture is selected from the group consisting of a $CH_4$ and $CO_2$ mixture, acidic natural gas containing $CH_4$ and $CO_2$, coal gas containing $CH_4$ and $CO_2$, landfill gas containing $CH_4$ and $CO_2$, biomass and sewage gas containing $CH_4$ and $CO_2$, flue and waste gas mixtures containing $CH_4$ and $CO_2$.

41. The process of claim 37 wherein the combined permeate from the membrane, hydrogen and carbon dioxide gas mixture is consumed as fuel-oxidant in a consecutive molten carbonate fuel cell.

42. The process of claim 41 wherein the flue hot gas emitted by the molten carbonate fuel cell is used for at least partial heating of the preceding far outer catalytic reaction zone.

43. The process of claim 41 wherein flue hot gas emitted by the molten carbonate fuel cell containing carbon dioxide, is recycled in the inlet of the preceding far outer catalytic zone for use as reactant in the reforming reaction.

44. The process of claim 41, wherein the molten carbonate fuel cell is of a cylindrical shape and its fuel anode encloses the cylindrical permeator by receiving and consuming directly as fuel the permeate hydrogen-carbon dioxide mixture, wherein the flux hot gas emitted by the fuel cell is used for at least partial heating of the enclosed far outer catalytic reforming zone.

45. The process of claim 37 wherein the reject exit-stream consisting of hydrogen and carbon monoxide enters as fuel gas feed in the anode of a consecutive solid oxide or molten carbonate fuel cell for continuous generation of electricity.

46. The process of claim 45 wherein the flue hot gas emitted by the solid or molten carbonate fuel cell is used for at least partial heating of the preceding far outer catalytic zone.

47. The process of claim 45 wherein the flue hot gas emitted by the solid oxide or molten carbonate fuel cell containing current dioxide, to be is recycled in the inlet of the preceding far outer catalytic zone for use as reactant in the reforming reaction.

48. The process of claim 37, wherein the reject exit stream rich in hydrogen and carbon monoxide after stream condensation is used as fuel feed in a gas engine or a gas turbine for continuous generation of electricity, wherein part or all of the permeate hydrogen and carbon dioxide coming out of the preceding membrane zone is fed as well in the engine or turbine in order to provide for supplementary hydrogen fuel.

* * * * *